United States Patent
Veres et al.

(10) Patent No.: US 8,955,249 B2
(45) Date of Patent: Feb. 17, 2015

(54) LIGHT ROD FOR ACCELERATING ALGAE GROWTH

(71) Applicant: BioVantage International, Inc., Golden, CO (US)

(72) Inventors: Michael Edward Veres, Highlands Ranch, CO (US); Ari Ma'Ayan, Lakewood, CO (US); Nicholas Arthur Rancis, Boulder, CO (US); Matthew Edward Donham, Colorado Springs, CO (US); David George Peter Deschenes, Aurora, CO (US); Gary C. Bjorklund, Pacific Grove, CA (US)

(73) Assignee: Biovantage International, Inc.

( * ) Notice: Subject to any disclaimer, the term of this patent is extended or adjusted under 35 U.S.C. 154(b) by 0 days.

(21) Appl. No.: 14/094,287

(22) Filed: Dec. 2, 2013

(65) Prior Publication Data

US 2014/0208640 A1  Jul. 31, 2014

Related U.S. Application Data

(63) Continuation of application No. 13/789,306, filed on Mar. 7, 2013, now abandoned, which is a continuation of application No. 12/943,904, filed on Nov. 10, 2010, now abandoned, which is a continuation of application (Continued)

(51) Int. Cl.
*A01G 7/04* (2006.01)
*A01G 33/00* (2006.01)
*F21V 8/00* (2006.01)

(52) U.S. Cl.
CPC .............. *A01G 7/045* (2013.01); *A01G 33/00* (2013.01); *G02B 6/0096* (2013.01)
USPC ....................................... 47/1.4; 47/58.1 LS

(58) Field of Classification Search
CPC ......... A01G 31/00; A01G 33/00; A01G 7/04; A01G 7/045; C12M 21/02; C12M 1/00
USPC .............................................. 47/1.4, 58.1 LS
See application file for complete search history.

(56) References Cited

U.S. PATENT DOCUMENTS 4,335,215 A  6/1982  Tolbert et al.
4,626,065 A * 12/1986  Mori .............................. 385/25

(Continued)

FOREIGN PATENT DOCUMENTS

JP        10-123328 A     5/1998
WO       2007098150 A2    8/2007

(Continued)

OTHER PUBLICATIONS

Ganzer et al. Integration of an Algal Photobioreactor Into an Environmental Control and Life Support System of a Space Station. Acta Astronautica 65. pp. 248-261. 2009.

(Continued)

*Primary Examiner* — Monica Williams
(74) *Attorney, Agent, or Firm* — Marsh Fischmann & Breyfogle LLP

(57) ABSTRACT

A light pipe for use in aqueous environments comprising an optical rod capable of total internal reflection, and disposed in the optical path of a light source such as a light emitting diode or other source. The optical rod has frosted and unfrosted portions, such that the light is propagated distally along the rod at the unfrosted portions, but a portion of the light is coupled out of the rod into the aqueous environment at each of the frosted portions. The relative sizes of the frosted portions are arranged so that substantially the same light power is coupled out of the rod at each frosted section, thus facilitating rapid and uniform growth of algae in the aqueous environment.

19 Claims, 17 Drawing Sheets

Light Rod Exploded View

Related U.S. Application Data

No. 12/943,911, filed on Nov. 10, 2010, now abandoned, which is a continuation of application No. 12/943,919, filed on Nov. 10, 2010, now abandoned, which is a continuation of application No. 12/943,922, filed on Nov. 10, 2010, now abandoned, which is a continuation of application No. 12/943,901, filed on Nov. 10, 2010, now abandoned, which is a continuation of application No. 12/943,914, filed on Nov. 10, 2010, now abandoned.

(60) Provisional application No. 61/280,847, filed on Nov. 10, 2009.

(56) References Cited

U.S. PATENT DOCUMENTS

| | | | |
|---|---|---|---|
| 4,657,677 A | | 4/1987 | Roubickek et al. |
| 4,724,214 A | * | 2/1988 | Mori .................... 435/292.1 |
| 4,900,669 A | | 2/1990 | Hatch et al. |
| 4,952,511 A | | 8/1990 | Radmer |
| 4,954,931 A | | 9/1990 | Hassler, Jr. |
| 5,151,347 A | * | 9/1992 | Delente et al. .................... 435/3 |
| 5,162,051 A | | 11/1992 | Hoeksema |
| 5,274,228 A | | 12/1993 | Kaplan |
| 6,509,188 B1 | | 1/2003 | Trosch et al. |
| 7,077,525 B2 | | 7/2006 | Fischer et al. |
| 7,824,904 B1 | | 11/2010 | Dimanshteyn |
| 7,879,236 B2 | | 2/2011 | Terry |
| 2003/0059932 A1 | | 3/2003 | Craigie et al. |
| 2003/0190742 A1 | | 10/2003 | Whiteman |
| 2003/0209489 A1 | | 11/2003 | Haerther et al. |
| 2005/0135104 A1 | | 6/2005 | Crabb et al. |
| 2005/0260553 A1 | | 11/2005 | Berzin |
| 2008/0009055 A1 | | 1/2008 | Lewnard |
| 2008/0268302 A1 | | 10/2008 | McCall |
| 2009/0029445 A1 | | 1/2009 | Eckelberry et al. |
| 2009/0126265 A1 | | 5/2009 | Rasmussen et al. |
| 2009/0230040 A1 | | 9/2009 | Limcaco |
| 2009/0291485 A1 | | 11/2009 | Shigematsu et al. |
| 2009/0320362 A1 | * | 12/2009 | Williamson et al. ............... 47/60 |
| 2010/0099151 A1 | | 4/2010 | Stroiazzo-Mougin et al. |
| 2010/0144019 A1 | | 6/2010 | Hsu |
| 2010/0200500 A1 | | 8/2010 | Rezania et al. |
| 2010/0267125 A1 | | 10/2010 | Erb et al. |
| 2011/0070632 A1 | | 3/2011 | Katoch et al. |
| 2011/0107664 A1 | | 5/2011 | Rancis et al. |
| 2011/0113682 A1 | | 5/2011 | Ma'Ayan et al. |
| 2011/0114556 A1 | | 5/2011 | Donham et al. |
| 2011/0117638 A1 | | 5/2011 | Veres et al. |
| 2011/0120944 A1 | | 5/2011 | Ma'Ayan et al. |
| 2011/0122645 A1 | | 5/2011 | Donham et al. |

FOREIGN PATENT DOCUMENTS

| | | |
|---|---|---|
| WO | 2008033573 A2 | 3/2008 |
| WO | 2008144583 A1 | 11/2008 |
| WO | 2010025345 A2 | 3/2010 |
| WO | 2010117720 A1 | 10/2010 |
| WO | 2010120611 A1 | 10/2010 |
| WO | 2011060107 A2 | 5/2011 |

OTHER PUBLICATIONS

Guterman et al. A Macromodel For Outdoor Algal Mass Production. Biotechnology and Bioengineering. vol. 35. pp. 809-819. 1990.

Ogbonna et al. A Novel Internally Illuminated Stirred Tank Photobioreactor For Large-Scale Cultivation of Photosynthetic Cells. Journal of Fermentation and Bioengineering. vol. 82, No. 1. pp. 61-67. 1996.

Ogbonna et al. Light Supply Coefficient: A New Engineering Parameter for Photobioreactor Design. Journal of Fermentation and Bioengineering. vol. 80, No. 4. pp. 369-376. 1995.

* cited by examiner

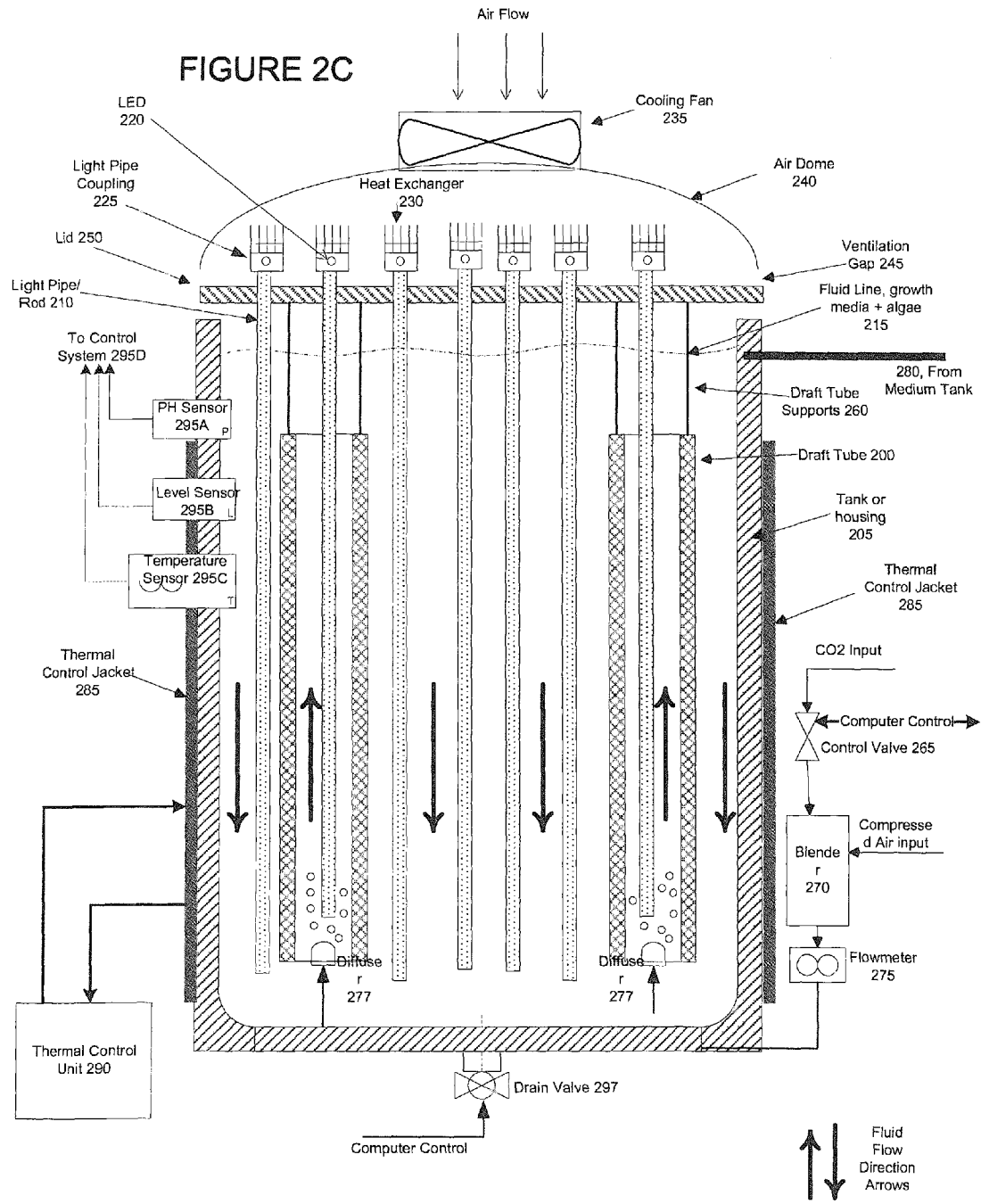

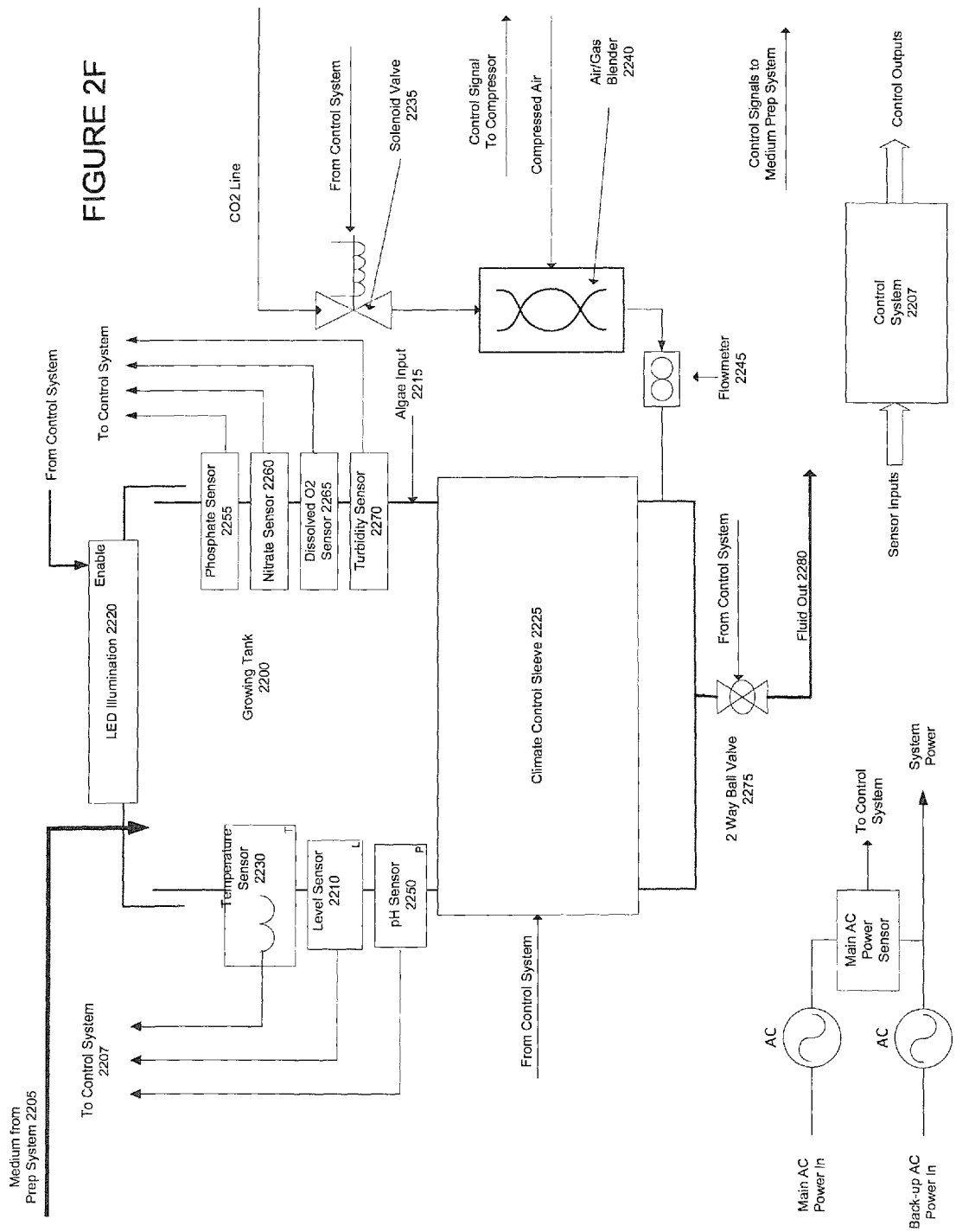

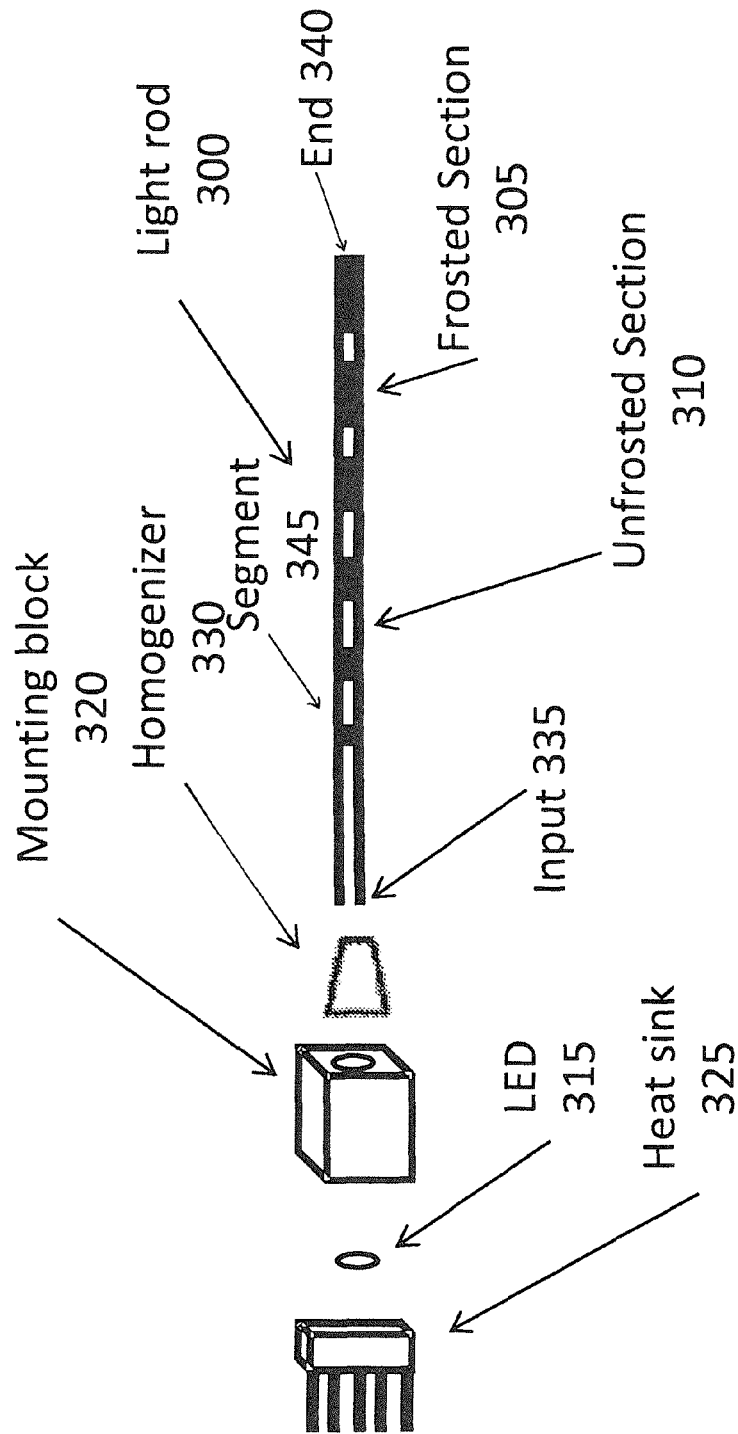
Figure 3A: Light Rod Exploded View

Medium Prep Process Flow

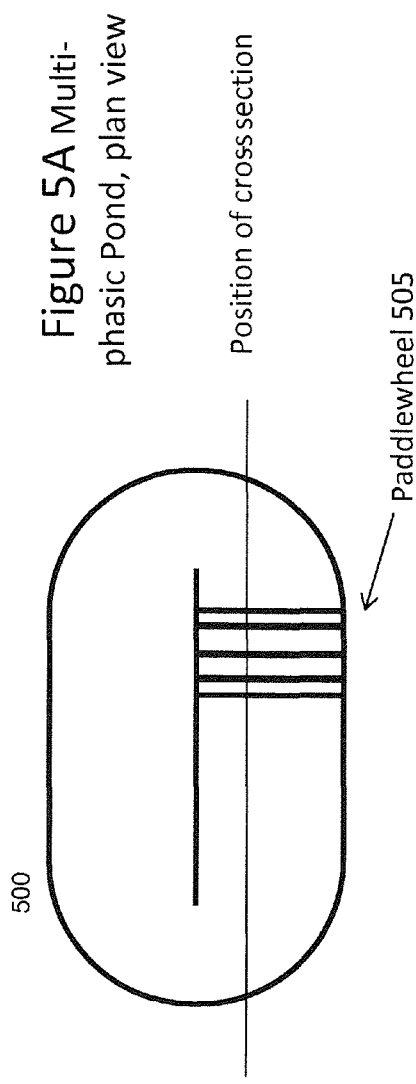
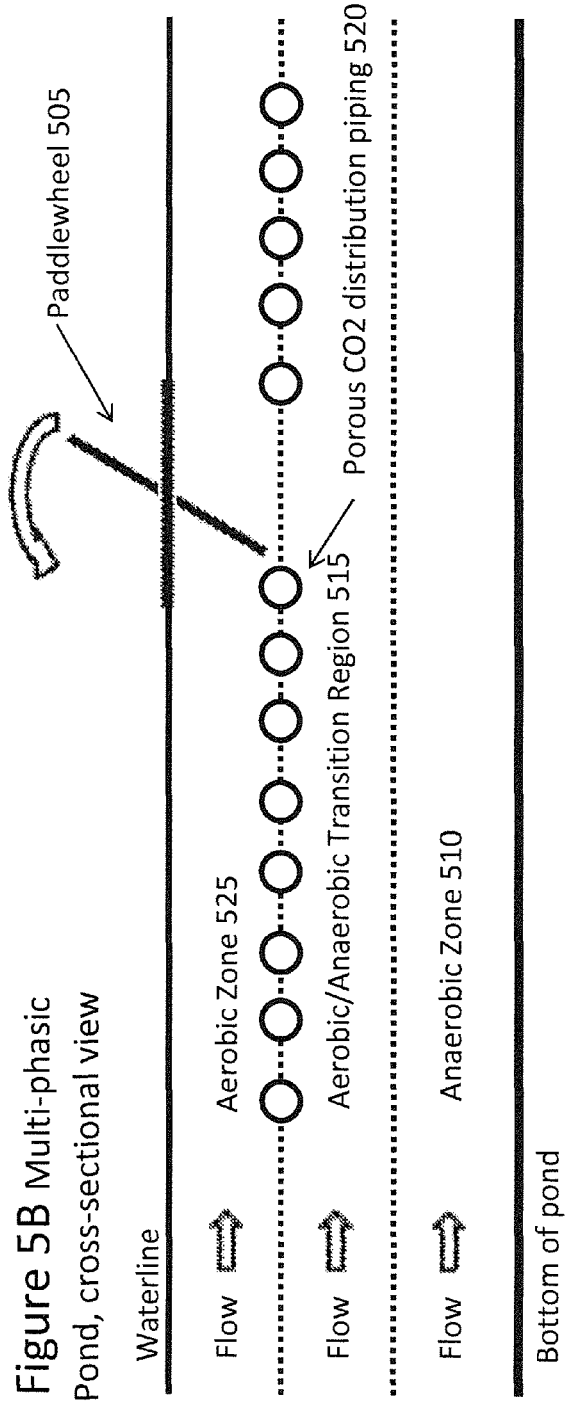

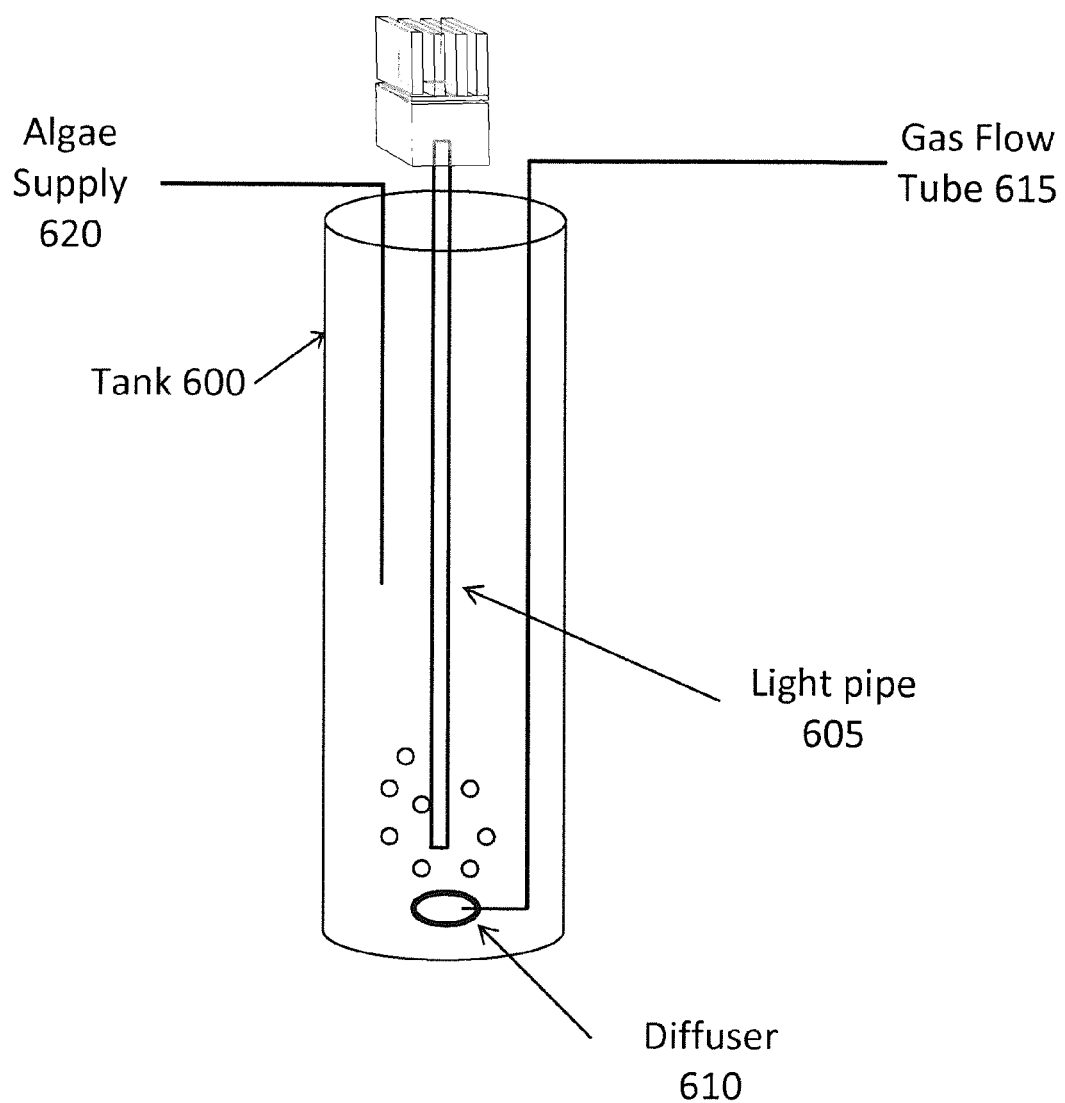
Figure 6 Internally lit bubble column

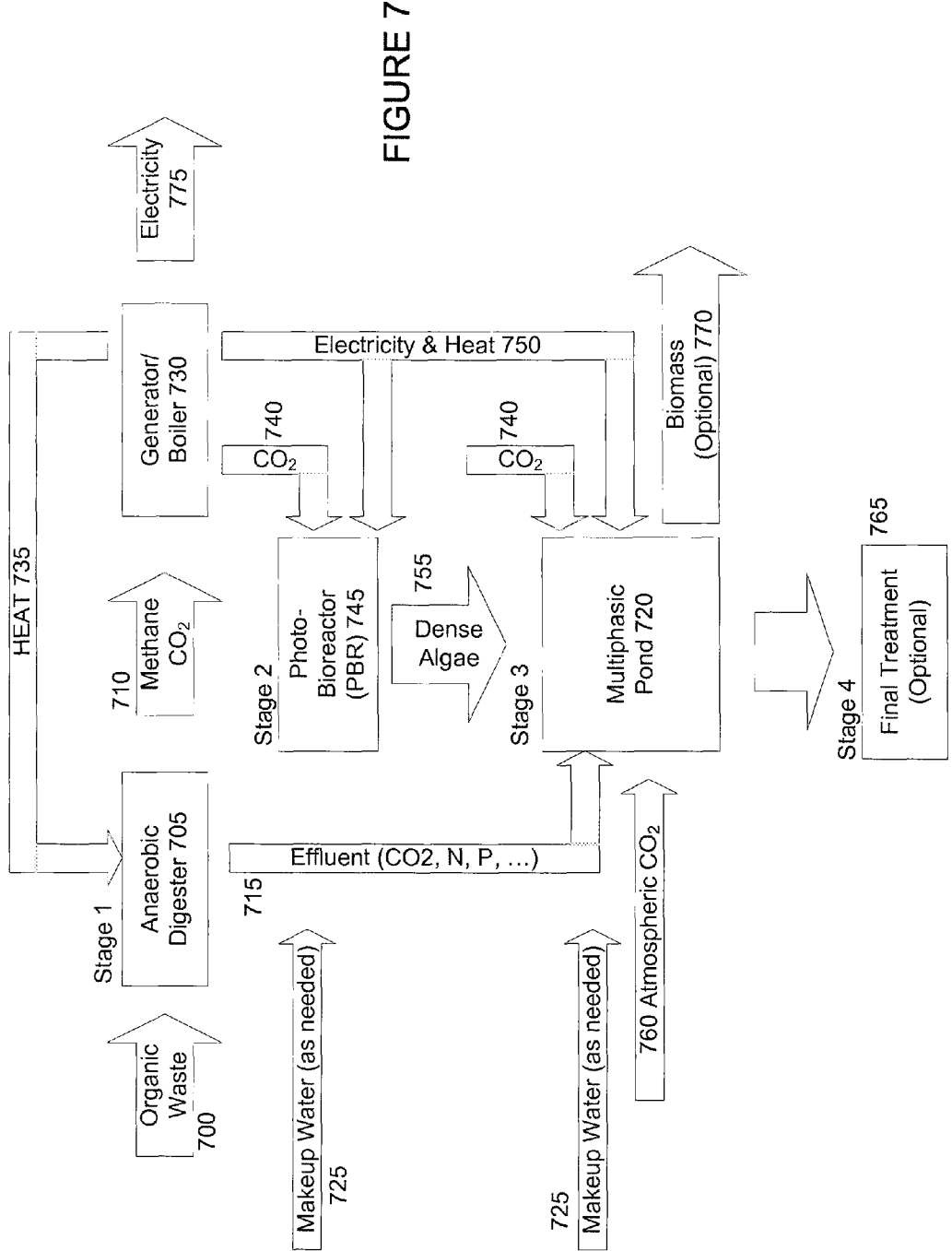

Concentrator Process Flow

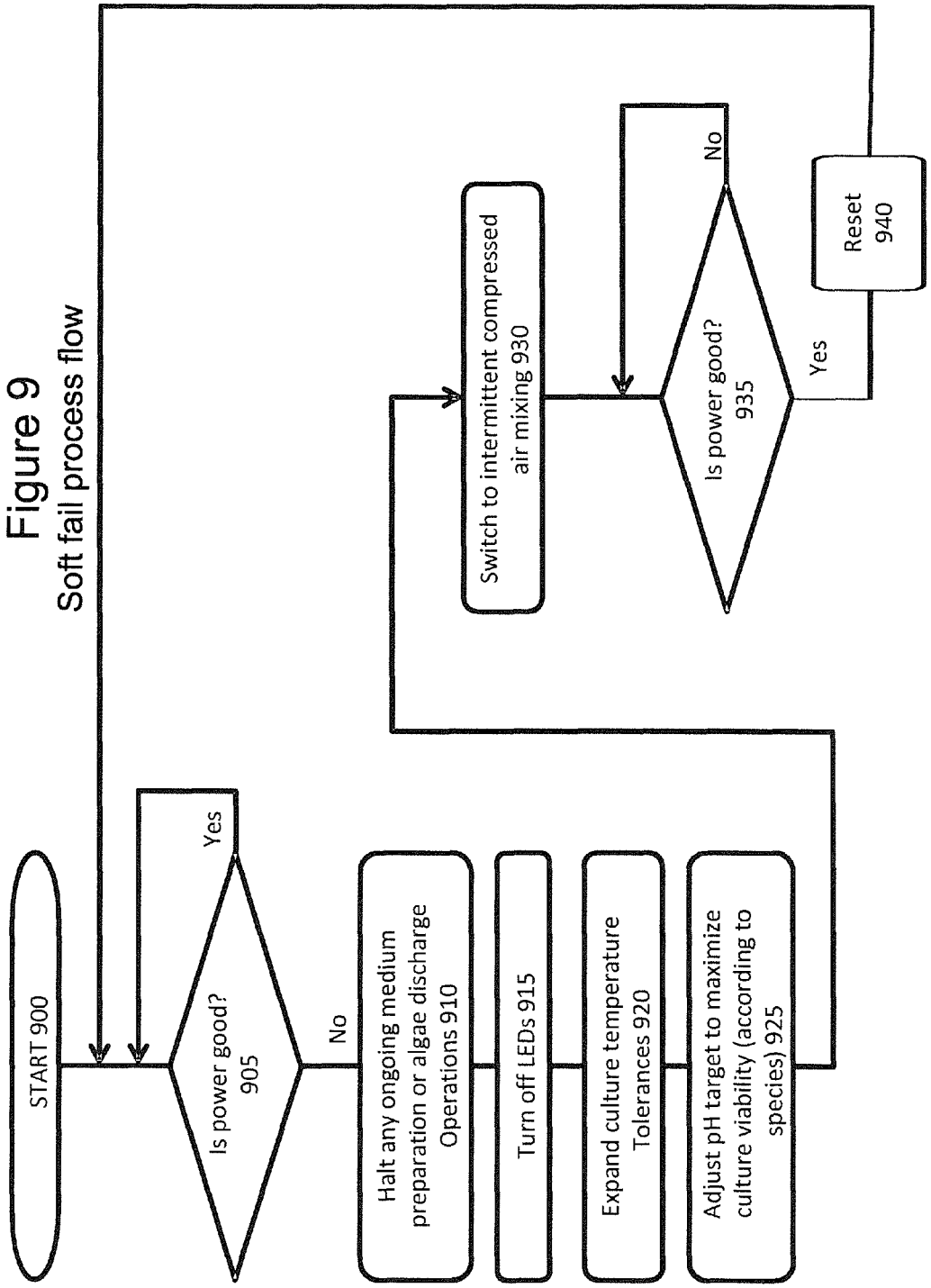

LIGHT ROD FOR ACCELERATING ALGAE GROWTH

CROSS-REFERENCE TO RELATED APPLICATIONS

This application is a continuation of U.S. patent application Ser. No. 13/789,306, filed Mar. 7, 2013. U.S. patent application Ser. No. 13/789,306 is a continuation of U.S. patent application Ser. No. 12/943,904, filed Nov. 10, 2010, which claims the benefit of U.S. Provisional Application No. 61/280,847, filed Nov. 10, 2009. U.S. patent application Ser. No. 13/789,306 is a continuation of U.S. patent application Ser. No. 12/943,911, filed Nov. 10, 2010, which claims the benefit of U.S. Provisional Application No. 61/280,847, filed Nov. 10, 2009. U.S. patent application Ser. No. 13/789,306 is a continuation of U.S. patent application Ser. No. 12/943,919, filed Nov. 10, 2010, which claims the benefit of U.S. Provisional Application No. 61/280,847, filed Nov. 10, 2009. U.S. patent application Ser. No. 13/789,306 is a continuation of U.S. patent application Ser. No. 12/943,922, filed Nov. 10, 2010, which claims the benefit of U.S. Provisional Application No. 61/280,847, filed Nov. 10, 2009. U.S. patent application Ser. No. 13/789,306 is a continuation of U.S. patent application Ser. No. 12/943,901, filed Nov. 10, 2010, which claims the benefit of U.S. Provisional Application No. 61/280,847, filed Nov. 10, 2009. U.S. patent application Ser. No. 13/789,306 is a continuation of U.S. patent application Ser. No. 12/943,914, filed Nov. 10, 2010, which claims the benefit of U.S. Provisional Application No. 61/280,847, filed Nov. 10, 2009. U.S. patent application Ser. Nos. 13/789,306, 12/943,904, 12/943,911, 12/943,919, 12/943,922, 12/943,901, 12/943,914, and U.S. Provisional Application No. 61/280,847 are incorporated herein by reference in their entirety for all that they disclose.

FIELD OF THE INVENTION

The present invention relates generally to wastewater treatment systems and methods, and more particularly relates to wastewater treatment systems utilizing anaerobic and aerobic microorganisms for bioremediation.

BACKGROUND OF THE INVENTION

The vast majority of the world's wastewater does not undergo treatment of any kind before being dumped into the nearest open water source. This has resulted in an international health crisis, where people die daily for lack of clean water. Unstable ecosystems caused by nutrient rich waste runoff are creating high rates of fish kill, ocean floor plant kill and large concentrations of pathogenic bacteria. This is a direct effect of lack of treatment or poor treatment and disposal of such waste streams. Effects such as disastrous algae blooms in open water sources from eutrophic conditions have drastically increased in the past decade and pose unprecedented environmental problems.

Typical prior art wastewater treatment systems typically employ mechanical aeration and chemical treatment. These systems are expensive to build and to operate, not solely because of the high energy costs incurred in the aeration process, but also because of the manpower required to operate the expensive machinery employed in such systems. Such mechanical/chemical treatment facilities, even those that are considered "state of the art," have a price tag in the millions and even up to hundreds of millions of dollars, making them so expensive that many communities, in the US and other parts of the developed world, have in the past been unable to afford such sewage treatment systems. As a result, the majority of the world's population lives with massive sewage pollution.

Bioremediation of wastewater has been proposed in the past. Such bioremediation systems typically employ a combination of aerobic and anaerobic processes. In particular, such prior art systems have generally proposed the use of anaerobic bacteria for digestion of organic matter and the release of biogas, combined with phototrophic organisms that produce oxygen to accelerate the breakdown of organic matter by aerobic bacteria. (At the same time, the aerobic bacteria produce carbon dioxide which is needed by the phototrophic organisms.) Anaerobic digestion kills most of the pathogenic bacteria found in raw sewage by depriving it of oxygen. In addition, the anaerobic bacteria are able to digest most of the biologically activating solids. Through this anaerobic digestion process, levels of Biological Oxygen Demand (BOD) and Chemical Oxygen Demand (COD) are greatly reduced, in addition to decreasing the amount of solid content in the waste. In this manner, the complementary nature of aerobic and anaerobic processes can be harnessed to break down organic material into its elemental forms without the use of 'heat, beat and treat' systems currently used in conventional, mechanical aeration/chemical treatment waste remediation facilities.

Algae has long been proposed as a suitable phototrophic organism for use in such bioremediation of wastes. One large project using such an approach is the St. Helena Wastewater Treatment plant in California, and other such plants have been put into service elsewhere in the world.

These solutions have demonstrated a number of desirable characteristics, but have had significant shortcomings. Because these prior art systems do not have a mechanism for controlling the algal specie(s) present, their algae cultures drift over time, often with unwanted outcomes. These undesirable outcomes include the growth of species that cannot be easily separated from the water at the end of processing; the proliferation of species that grow well during "normal" conditions, but are unable to grow in the case of process excursions, e.g. an influx of an industrial pollutant; or the proliferation of algaie species that grow well, but do not perform all of the desired remediation.

Further, absent a mechanism for active replenishment of the algae, wash-out events (e.g. from a rainstorm) can severely dilute the algae culture density, such that the system is unacceptably slow to return to an effective culture density.

Thus, there has been a long-felt, and growing, need for a wastewater remediation system and method that is cost effective while offering an efficient, stable remediation approach.

SUMMARY OF THE INVENTION

The present invention provides a system and method for efficient, cost-effective bioremediation of wastewater and other contaminated fluid streams. In one aspect, the invention includes a photobioreactor (hereinafter sometimes "PBR" for simplicity) for growing high concentrations of algae. The PBR comprises a tank having specially configured light pipes distributed therein to cause high density algae growth substantially throughout the tank. Fluid flow in the tank is maintained at a level low enough to prevent damage to the algae while at the same time allowing the fluid to circulate throughout the tank.

Another aspect of the invention comprises a medium system for supplying nutrients to the PBR or other growth system. The nutrient system can comprise a plurality of separately selected components which are then assembled into a nutrient stream through a plurality of metering pumps, or, in some embodiments, can be derived from a portion of the effluent of an anaerobic digester. In some embodiments, the anaerobic digester forms a first stage of the overall bioremediation system. The anaerobic digester stage, aside from providing a stream rich in micro and macronutrients, also provides significant amounts of $CO_2$ to the PBR, which assists in the growth of algae in the PBR. In addition, the anaerobic digester generates significant quantities of biogas, which can be utilized by a conventional biogas-powered generator to produce at least a portion of the electricity required to operate the bioremediation system of the present invention. Carbon dioxide from the biogas can be used in the lagoon or pond to accelerate algae growth before, after, or instead of burning of the biogas. In the case where the biogas is burned, the resultant heat energy can be used to warm the water in the lagoon, accelerating various of the desirable biological processes ongoing there.

Yet another aspect of the invention comprises a remediation lagoon or pond, typically although not necessarily using a raceway design, where the remediation pond is fed high-density algal inoculum from the photobioreactor system. A portion, in many cases the majority, of the effluent from the anaerobic digester stage provides the incoming fluid stream to be remediated in the remediation pond. In some embodiments, the remediation pond can be a multi-phasic pond utilizing multiple biological capabilities enabling it to process the residual $CO_2$, nitrogen and phosphorus remaining in the effluent from the anaerobic digester stage. In at least some embodiments, the multi-phasic ponds comprise a plurality of horizontal strata, for example: aerobic at the surface, aerobic/anaerobic, and anaerobic on the bottom. The overall function is to remove residual nitrogen and phosphorus in the system through the use of phototrophic microorganisms, while simultaneously consuming $CO_2$ and creating 02 to aid in the breakdown of residual effluent from anaerobic digestion. These ponds can be sized individually for each implementation or user application.

THE FIGURES

FIG. 2C shows an alternative embodiment of a photobioreactor having a plurality of draft tubes.

FIG. 2F shows in flow diagram form the operation of the photobioreactor in accordance with an aspect of the invention.

FIG. 3A shows an embodiment of a light rod as used in an embodiment of the photobioreactor of FIGS. 2A and 2B.

FIGS. 5A-5B show an embodiment of a multiphasic pond in accordance with an aspect of the invention.

FIG. 6 shows an embodiment of a bubbler in accordance with an aspect of the invention.

FIG. 7 shows in schematic form an alternative embodiment of a wastewater remediation system in accordance with an aspect of the invention.

FIG. 9 illustrates in generalized flow diagram form an embodiment of a soft fail process in accordance with an aspect of the invention.

DETAILED DESCRIPTION OF THE INVENTION

Figure 1:
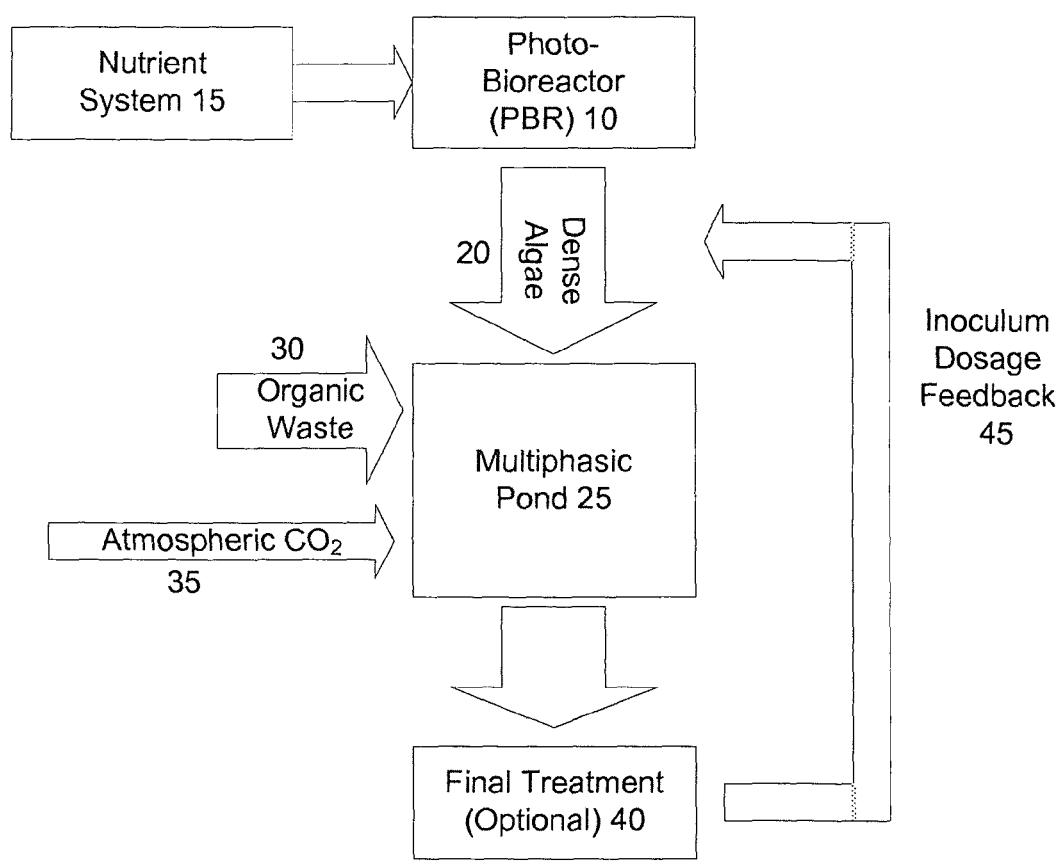
FIG. 1 shows schematically an embodiment of a water remediation in accordance with one aspect of the invention.

Referring first to FIG. 1, a bioremediation system in accordance with one aspect of the invention comprises a photobioreactor or PBR 10, described in greater detail hereinafter, which receives a nutrient stream from a nutrient system 15. The PBR provides an optimized environment for the growth of highly concentrated algae. The algae from the PBR 10 is supplied via a conduit 20 to a wastewater pond or lagoon 25, which, in some but not necessarily all embodiments, is a multiphasic pond as discussed in connection with FIG. 5. The pond or lagoon 25 receives organic waste 30, and, in many embodiments, can also receive atmospheric $CO_2$ as indicated at 35.

The wastewater pond or lagoon 25, which can cover less than an acre to tens or hundreds of acres and could even be an open water area such as a lake or bay given sufficiently large algae supplies, comprises in some embodiments a relatively shallow pond having at least one remediation strata and, in the case of multiphasic ponds, a plurality of strata. As explained in greater detail hereinafter, the algae from the PBR are provided to the lagoon in doses sufficient to inoculate the lagoon; that is, to provide enough algae to the lagoon that the natural conditions in the lagoon will permit the algae to thrive for a reasonable period of time, propagating naturally. The algae typically, although not necessarily, operate symbiotically with bacteria with which they commingle in the lagoon. In the embodiment in which both algae and bacteria are present, bacterial action reduces BOD and TSS (Total Suspended Solids) and reduces nitrogen while producing $CO_2$. Compared to the bacteria, algae reduce BOD, TSS, and nitrogen to a lesser extent, and substantially reduce phosphorus, all while producing oxygen. This symbiotic relationship, in which the bacteria produce $CO_2$ consumed by the algae as the algae produce $O_2$ consumed by the bacteria, significantly accelerates the activity of both organisms. (In addition, some $CO_2$ and $O_2$ come in from the atmosphere.)

By moving the wastewater through the pond or lagoon at a suitable rate, to ensure sufficient mixing, to maintain homogeneity of the water chemistry & temperature, as well as maintain suspension of the algae and bacteria, the outflow from the pond 25 is substantially remediated. Optionally, a final treatment 40 can be provided, in the form of an algae separation step and/or a maturation or clarification stage. An algae separation step permits collection of the algae biomass for value-added applications (e.g. fertilizer). A maturation pond, constructed wetland, or similar solution would promote settling of the algae and further reduction of nitrates and phosphates. In addition, in some embodiments automated feedback, indicated at 45, can be provided which determines the water quality of the outflow and accordingly adjusts the level of inoculation to ensure that proper levels of water quality are achieved and maintained. In systems where no final treatment step is performed, the water quality of the output of the pond 25 is used to provide feedback.

Figure 2A:
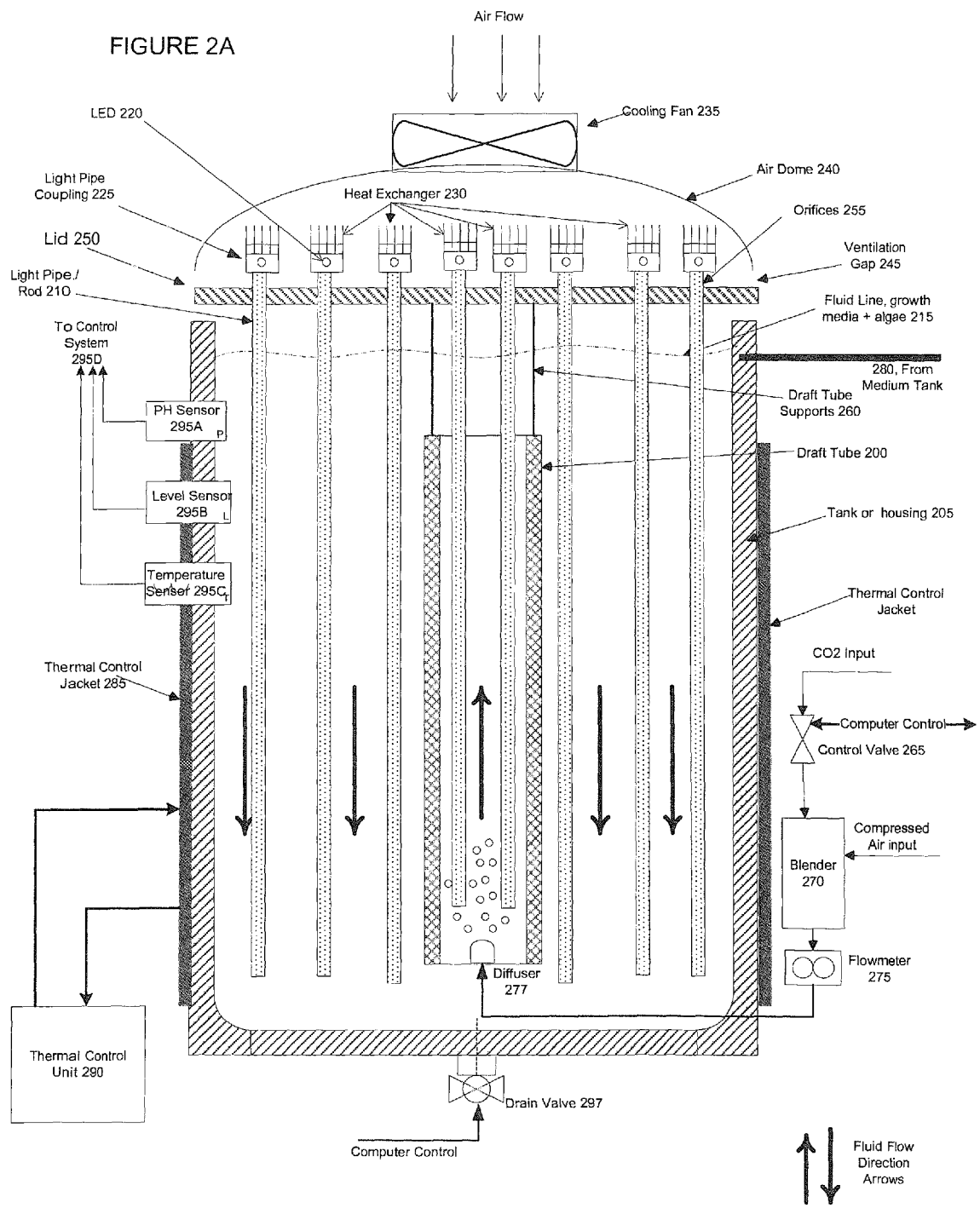
FIGS. 2A and 2B show, respectively, a cross-sectional side view and an exploded view of an embodiment of a photobioreactor having a single draft tube in accordance with one aspect of the invention.
Figure 2B:
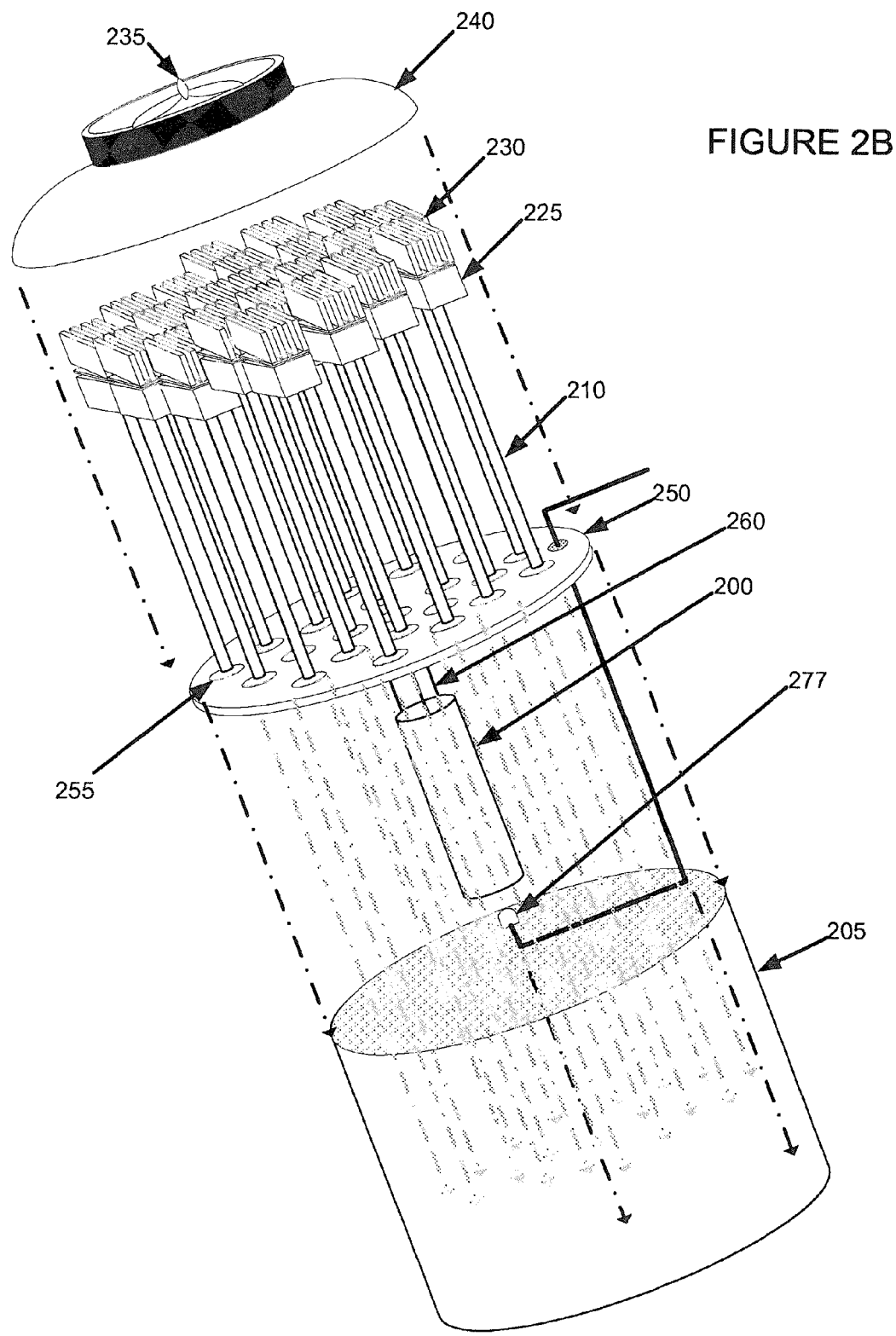

Referring next to FIGS. 2A and 2B, an embodiment of the photobioreactor of the present invention can be better understood, shown in cross-sectional and exploded perspective views, respectively. A draft tube 200 is centrally disposed within a housing or tank 205. In an embodiment, the tank has a useful capacity of about 50 gallons with a diameter of approximately 22 inches, while the draft tube has a capacity of approximately 4.5 gallons and a diameter of approximately seven inches. The relative volumes and diameters of the tank 200 and draft tube 205 can vary substantially, although in at least some embodiments a draft tube diameter of five to twenty-five percent of the tank diameter has been found useful. In some embodiments, the tank is sized to have a height/diameter ratio approximately 1.5:1, although this ratio is not limiting and the relative dimensions of the tank can vary significantly.

Arranged within the draft tube are one or more light rods or pipes 210, as described in greater detail in connection with FIG. 3A. A plurality of light pipes 210 are also arranged within the housing 205 and around the outside of the tube 200. The exact number of light pipes 210 both within the diffusion tube and arranged outside of the diffusion tube can vary depending upon the size of the tank and the particular implementation of the invention. In general, it is desirable to space the light pipes apart by approximately twice the absorption distance of the light emitted from the light pipes. In an embodiment, for example, the light pipes are spaced approximately 10-15 centimeters apart, although the exact dimensions can vary depending on numerous factors, including the type of algae, the level of algae concentration desired for a particular PBR, and the wavelength and power of the LED's providing light to the light pipes.

The housing 205 contains growth media 215, as described in greater detail in connection with FIG. 4, together with algae selected to be appropriate for the particular remediation system. Light of one or more preselected wavelengths, appropriate to facilitate growth of the selected algae, is supplied by one or more LED's 220 or similar light sources associated with each of the light pipes 210. While LED's are the preferred light source for many embodiments, other light sources are acceptable for some embodiments, including lasers, diode lasers, diode pumped solid state lasers, diode pumped fiber lasers, high intensity discharge lamps and other lamps, infrared sources converted to wavelengths appropriate for the particular strains of algae, or even sunlight coupled to the light pipes using heliostats or similar devices. For convenience, the light source will be described herein as "LED", but is to be understood as meaning any light source appropriate for the particular implementation of the invention. The LED's 220 are disposed at the top thereof, typically above the top of the media, where light emitted from the LED's is transmitted down the light pipe through a coupling 225. In some embodiments, multiple LED's can be used to emit light of different wavelengths along a single rod, a single LED can emit multiple wavelengths along a single rod, or some rods can have LED's emitting a first wavelength while other rods have LED's emitting other wavelengths. In addition, in some embodiments various dyes can be used in the rods to convert light of one wavelength to another more appropriate for the strains of algae being grown in the tank.

Each of the light pipes can also include a homogenizer or mixer, as shown in FIG. 3A, to improve spatial uniformity in the light pipes, although the homogenizer is not required for all implementations. Each of the LED's can have associated therewith a heat sink or heat exchanger 230, to keep the LED's at an appropriate operating temperature. In at least some implementations, it is desirable to cool the LED's sufficiently that heat from the LED's does not adversely affect the growth of the algae within the tank. To facilitate cooling of the LED's, one or more fans 235 can be positioned at an orifice in an air dome 240, with a ventilation gap 245 disposed between the air dome 240 and a tank lid 250 to allow air to exit. In general, the purpose of the light pipes 210 is to transit light from the LED's as uniformly as possible throughout the tank, to encourage algae growth at all levels within the tank, while not transmitting the heat from the LED's into the tank and not impeding fluid flow within the tank.

In an embodiment, the light rods are supported by a tank lid 250, which has orifices 255 therethrough. Each of the light pipes 210 slides through an orifice 255 so that the majority of the light pipe fits into the tank 205. The lid can also provide a connection point for one or more supports 260 for the draft tube 200, so that the top of the draft tube is maintained somewhat below the surface of the liquid in the tank, and the open bottom of the draft tube is maintained above the bottom of the tank.

To maximize the concentration of algae within the growth medium in the tank, the algae are typically moved or stirred gently within the tank. One technique for facilitating such slow movement is to blend $CO_2$ or other gas (depending on what algae is being cultured and for what purpose) with compressed air via a computer controlled valve 265 and blender 270. In some embodiments, no compressed air is used. Depending upon the particular implementation, the bubbled gas can be inert with respect to the growth medium and the culture being grown, or it can promote the growth of the culture such as by providing a nutrient, or it can otherwise regulate conditions in the tank such as by changing pH. The combined stream is supplied to the bottom of the draft tube 200 via a flowmeter 275 and a diffuser 277, where the diffuser operates to convert the gas stream into gas bubbles sized to be suitable for providing movement of the algae. The bubbles of gas mixture entrain the growth media and move algae in the draft tube upward as indicated by the upward flow arrows. In an embodiment, typical bubble size is on the order of 1 mm, but can vary significantly, in a range of 0.2 mm to 3 mm, or more.

Because the top of the draft tube is below the surface of the liquid, and also suspended above the bottom of the tank 200 preferably at a distance that facilitates a vacuum effect in at least some embodiments, the algae and growth media flow over the top of the draft tube and move downward within the portion of the tank outside the draft tube, as indicated by the downward flow arrow. In an embodiment using a single draft tube, a gas flow rate of 0.1-0.2 cubic feet per minute provides sufficient movement of the algae, although this flow rate is not intended to be limiting. This movement promotes homogeneity of the growth medium within the tank, prevents settling, and also facilitates the algae moving along the length of the light rods, so that the algae are relatively uniformly illuminated by the light emitted from the light rods throughout the volume of the tank 205, thus yielding relatively uniform growth throughout the tank, rather than merely at the surface as found in prior art systems. Additional growth medium can be supplied as necessary from a medium tank, as discussed in connection with FIG. 4, via tube 280A, while seed amounts of algae are supplied via tube 280B or through an orifice in lid 250. The junction of the walls and bottom of the tank can be rounded to facilitate smooth movement of the algae and to prevent algae from clogging at what would otherwise be a sharp corner, although such rounding is not necessary in all embodiments.

To promote good algae growth, the temperature of the growth media is controlled by means of a thermal control jacket 285, the temperature of which can be regulated by thermal control unit 290. The thermal control jacket can, for example, be formed with tubes therethough for heating or cooling fluid flow, or can be comprised of polymer heating/cooling material. In addition, pH, level, and temperature, indicated by sensors 295A-C, are monitored by control system 295D, typically a computer (not shown.) Once the algae concentration in the tank has reached the desired level, a computer-controlled drain valve 297 permits the algae to be transferred to a lagoon or pond seen in FIG. 1 to facilitate the remediation process. In some embodiments, algae concentrations of less than 50 mg/L up to 5000 mg/L or more can be achieved, with concentrations from 50 mg/L to 1000 mg/L being easily obtainable.

It will be appreciated that, while a single draft tube has been shown in FIGS. 2A-2B, multiple draft tubes can be used and may be desirable in tanks having a larger diameter, as shown in FIG. 2C. In general, having a plurality of smaller diameter draft tubes distributed around a larger tank will provide better fluid flow, especially near the edge of the tank, than a single tube of equivalent flow in the middle of a tank. In an embodiment, a gas flow of approximately 0.1 to 0.2 cubic feet per minute per draft tube provides sufficient stirring and movement of the algae and growth medium within the tank, where the combined diameters of the draft tubes comprises approximately five to twenty-five percent of the total surface area of fluid within the tank.

In the alternative embodiment of FIG. 2C, which is a cross-sectional view of a photobioreactor in which like numerals refer to like elements from FIG. 2A, a plurality of draft tubes 200 are disposed within the tank 205. Although only two such draft tubes 200 are shown, the design illustrated can accommodate a large range of draft tubes. Thus, for example, between one and four draft tubes are desirable for some embodiments where the tank is approximately 150 gallons, while an embodiment using a 300 gallon tank uses five draft tubes. The foregoing numbers are exemplary only and are not limiting. In general the number and placement of the draft tubes is intended to facilitate appropriate upward and downward flow of the algae-laden medium as described before in connection with FIGS. 2A-2B, where the algae is permitted to grow throughout the volume of the tank, rather than just at the surface as in prior art designs.

Figure 2D:
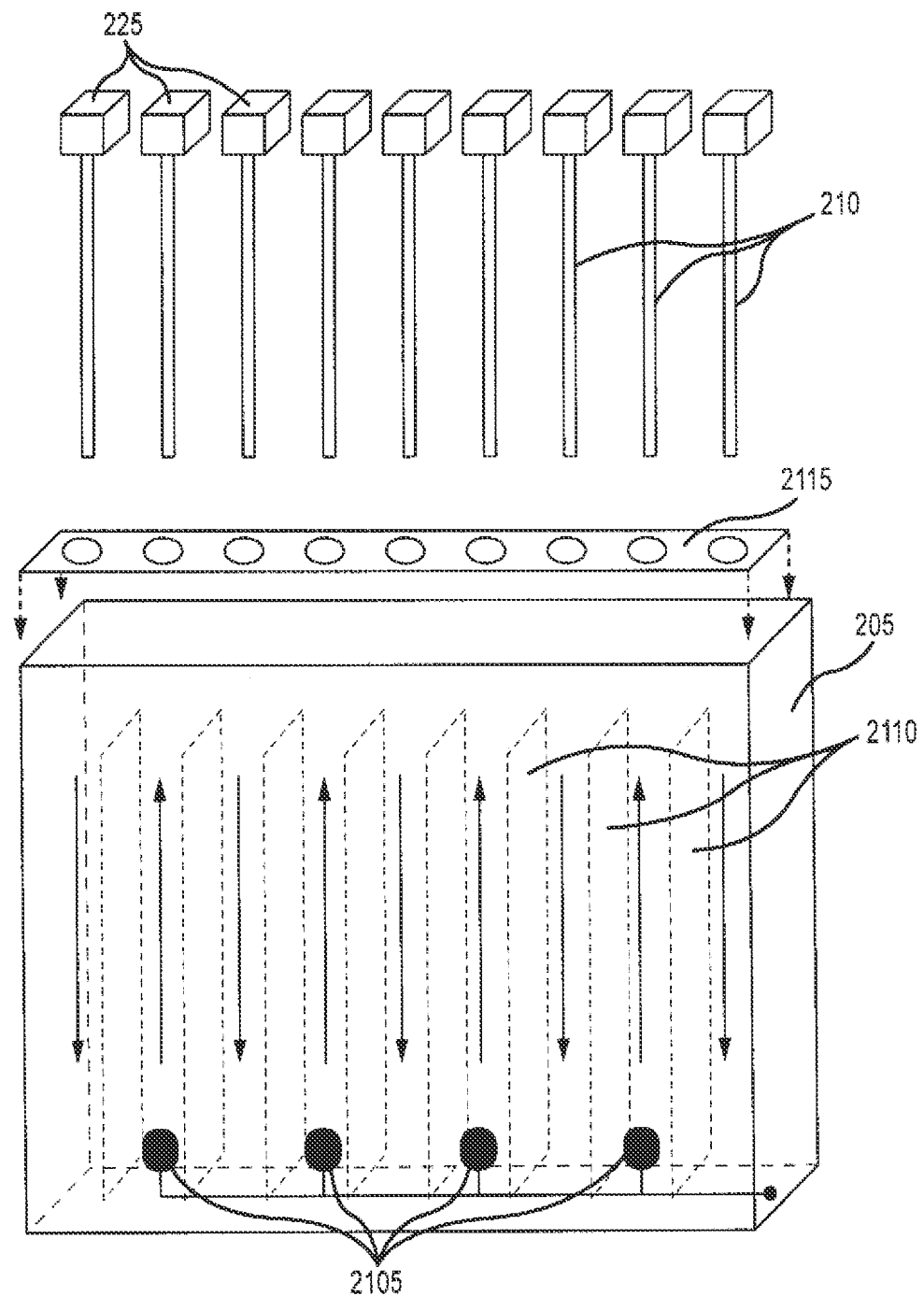
FIG. 2D shows another embodiment of a photobioreactor utilizing parallel plates with light rods in accordance with an aspect of the invention.

Referring next to FIG. 2D, which shows in perspective view with a transparent front wall a still further alternative embodiment of the PBR shown in FIG. 2A, it will be appreciated that the shape of the tank need not be round, and in fact can be any shape that permits sufficient light to reach the volume of algae growing in the medium. For clarity, elements with like functionality are again shown with the same reference numerals used in FIG. 2A, and, for clarity, many elements with identical functionality to those discussed in connection with FIG. 2A are omitted. Thus, the perimeter of the tank 205 shown in the embodiment of FIG. 2D is rectangular, with one or more baffles 2100 arrayed within the tank and extending from below the surface of the fluid to a distance above the bottom of the tank. The baffles thus create spaces having the same functionality as draft tubes 200. By placing diffusers 2110 with appropriate gas flow at the bottom of alternating baffled spaces, the desired upward and downward flows are created within alternating baffled spaces in the tank, as shown by the flow arrows. As with the PBR of FIG. 2A, a plurality of light pipes are disposed within the tank through a lid 2115. Although a linear array of light pipes 210 is shown in FIG. 2D, it will be apparent that the number and placement of the light pipes will vary with the dimensions of the tank 200, and need not be linear.

It will also be understood, from the description of FIGS. 2A-2C, that the wall-to-wall baffles shown in FIG. 2D are not required in all embodiments, and instead can be replaced with draft tubes as shown in FIGS. 2A-2C. In addition, the width of the tank can be varied as desired, with multiple draft tubes and multiple light pipes arrayed in accordance with the teachings given in connection with FIGS. 2A-2C. It will also be appreciated that, in some embodiments, light pipes can be placed in the corners of the tank, to prevent a fall-off in illumination at the corners, although such positioning could in some instances result in a less efficient use of the light from the corner light pipes. Adding a reflector behind the light pipe can reduce the loss. In addition, with light pipes positioned in the corners, the fluid flow in the corners is decreased and dead spots may occur.

Figure 2E:
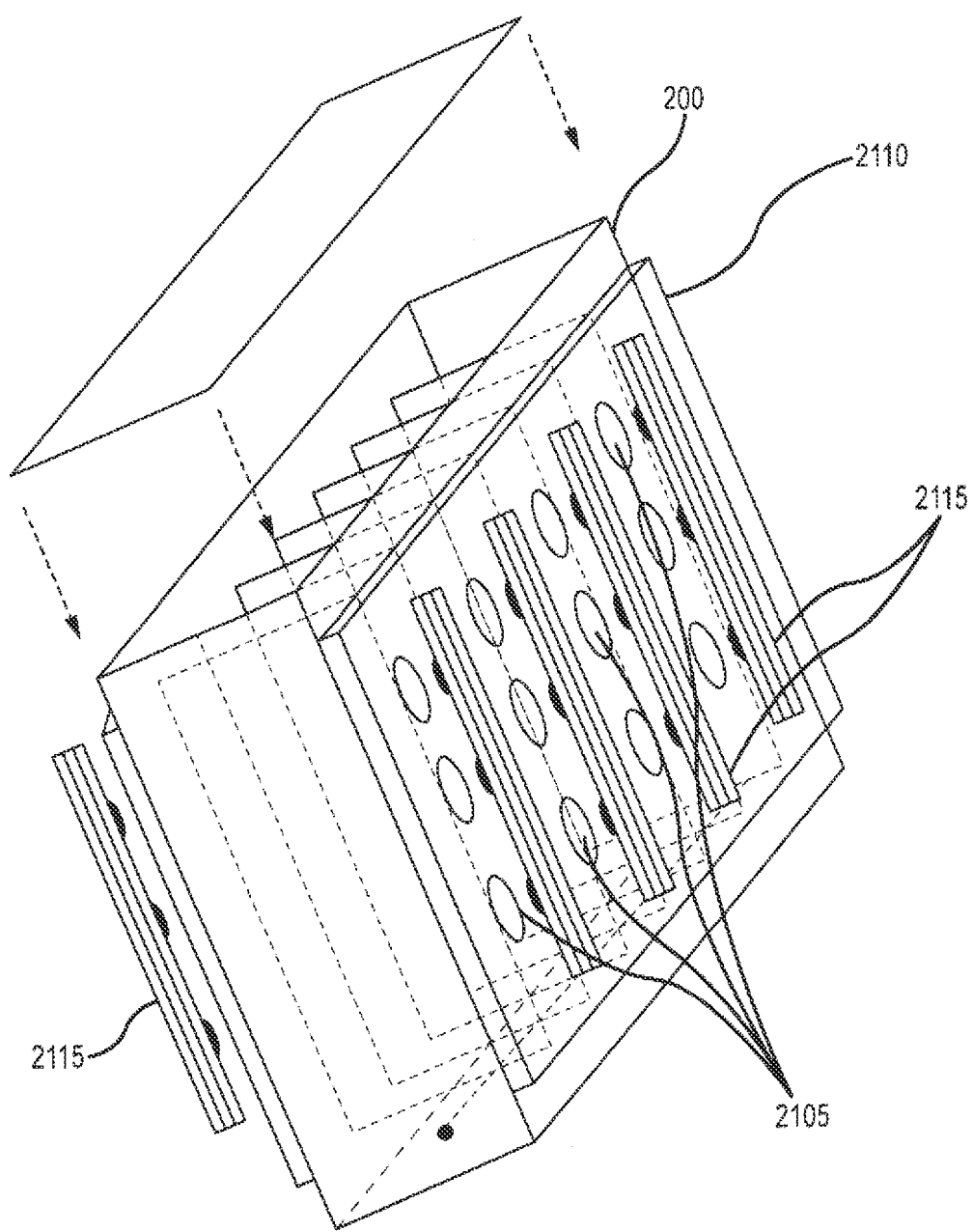
FIG. 2E shows an alternative embodiment of a photobioreactor utilizing parallel plates and external illumination.

Turning next to FIG. 2E, which shows a still further alternative embodiment of a PBR in accordance with an aspect of the invention, in some embodiments the light pipes 210 can be replaced with externally positioned LED's or equivalent light sources 2105. A thermal jacket 2110 is still provided, with orifices therethrough to accommodate the placement of the LED's 2105. Heat sinks 2115 are provided in at least some arrangements, and a cover [not shown] can be provided to control the air flow through the heat sinks, effectively creating a plenum. As with the design of FIG. 2D, baffles or draft tubes are disposed within the tank to create the appropriate flow of the algae and growth medium. The remaining elements of FIG. 2A (such as light pipes, controls, etc.) are not repeated in FIG. 2E for clarity, but would be included as appropriate in implementations of the embodiment shown in FIG. 2E. Since the light sources 2105 are external for the embodiment of FIG. 2E, the width of the tank is preferably constrained to ensure good illumination throughout the volume of the algae and medium flowing within the tank, and thus the width of the tank is typically at most a few inches. In at least some embodiments, LED's 2105 are disposed on both sides of the tank.

Referring next to FIG. 2F, the process flow for growing algae within the PBR's shown in FIG. 2A-2D can be better appreciated. Growth medium is supplied to the growing tank 2200 via tube 2205 from the medium preparation system (FIG. 4), either manually or under computer control 2207, as indicated by a level sensor 2210. Seed amounts of the selected species, one or more, of algae are added via tube 2215, again either manually or under computer control, or through one of the orifices in the tank lid prior to inserting the associated light pipe. Illumination 2220 is enabled from the control system, and the climate control sleeve 2225, or thermal jacket, brings the growth medium in the tank to a temperature appropriate for growing the algae within the tank, as monitored by temperature sensor 2230. The control system blends gases such as $CO_2$, air, nitrogen, or other gases, via solenoid valve 2235 and blender 2240, and throttles the volume of gas supplied to the tank via flowmeter 2245. The volume of gas is controlled by the control system both for purposes of setting the pH, as monitored by pH sensor 2250, and for the purpose of ensuring proper flow within the tank. Depending upon the constituents in the growth medium, the species of algae, and the bioproducts desired to be produced by the algae, various other sensors are monitored by the control system, for example phosphate levels 2255, nitrate levels 2260, dissolved $O_2$ 2265, and turbidity 2270. In addition to turbidity as a method for monitoring culture density, a colorimeter and/or a chlorophyll fluorescence probe can be used. When it is desirable to remove the algae and associated bioproducts from the tank, either manually or via the control system a valve 2275 is opened and the algae-laden fluid is removed from the tank via outlet 2280, either to be supplied to bioremediation lagoons or ponds, or otherwise used or disposed of.

Figure 3B:
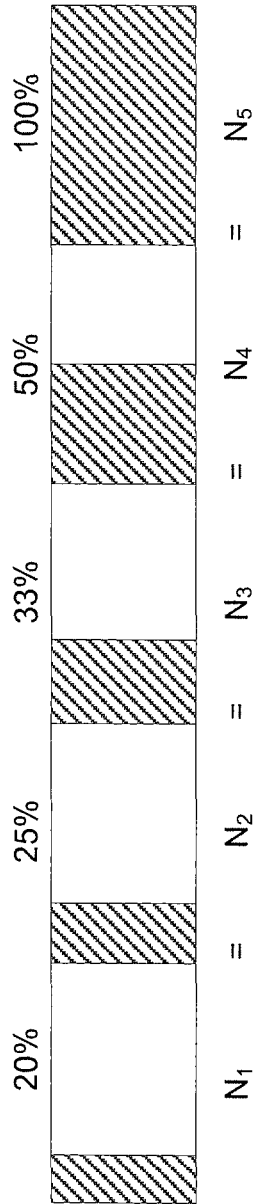
FIG. 3B shows a first alternative embodiment of a light rod in accordance with the invention.
Figure 3C:
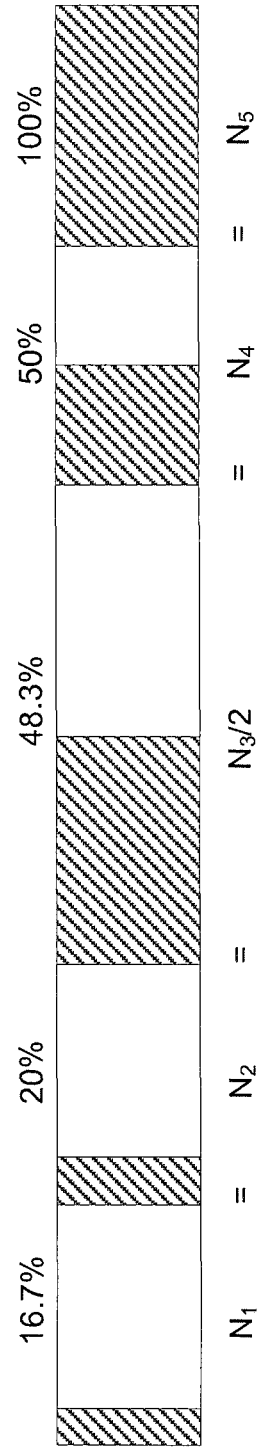
FIG. 3C shows a second alternative embodiment of a light rod in accordance with the invention.

Referring next to FIGS. 3A-3C, various embodiments of the light pipe of the present invention can be appreciated in greater detail. Referring first to FIG. 3A, an exploded view of an embodiment of a light pipe is shown. A clear rod 300, sized of a length to permit the rod to reach substantially to the bottom of a tank of a photobioreactor, comprises a series of alternating frosted and unfrosted sections 305 and 310. The rod 300 is typically comprised of acrylic or other polymer, or any other suitable material which is optically clear at the wavelength of the light emitted by one or more LED's 315 and capable of having a surface texture created on portions thereof to create the frosted and unfrosted sections 305 and 310. As noted before, the LED's can be of multiple wavelengths, with different wavelengths emitted from each rod, or all rods emitting multiple wavelengths, or all rods emitting the same wavelength. It is noted that, while the foregoing describes a single wavelength, those skilled in the art will recognize that, in this context, "wavelength" is more accurately a wavelength band, as LED's emit a spectral spread, where the center wavelength is described as the "wavelength" of the LED. Also, as noted previously, dyes can be used in or on the rods to convert light of a wavelength generated by the LED's to light of a different wavelength suited to the algae.

The LED's 315 are mounted in a mounting block 320, which is thermally coupled to a heatsink 325 depending on the heat generated by the LED's 315. In some embodiments, it is desirable to provide spatially uniform light from the LED's to the rods 300, in which case a homogenizer 330 can be disposed in the optical path between the output of the LED's 315 and the input 335 of the rod 300. The homogenizer 330 typically has a non-circular cross-section throughout most or all of its length and utilizes internal reflection, including total internal reflection depending upon the material used, to create spatial uniformity of the light at the output of the homogenizer. The input face 335 of the homogenizer 330 is typically sized so that its input dimensions are substantially matched to the output of the LED's, thereby allowing the homogenizer to capture all or nearly all of the light output of the LED's. Similarly, the dimensions of the output face of the homogenizer are sized to substantially match the input of the rod 300, so that the loss of light at the transition from the homogenizer to the rod is minimized. It is not necessary that the output of the homogenizer be congruent with either the output of the LED's or the input of the light rod. In the case of the output of the LED's, the input face of the homogenizer can be larger. In the case of the input to the light rod, the output face of the homogenizer can, for example, be a square with its corners intersecting or contained within the circular face of the rod 300, or can be any other shape reasonably contained within but substantially covering the input face of the rod 300, although homogenizers with an odd number of sides offer improved performance in some instances.

In an important aspect of the light rods 300, the arrangement of frosted and unfrosted sections 305 and 310 control the location along its length and amount of light emitted from the rod. Light entering the input to the rod is transmitted along the unfrosted sections by total internal reflection. However, at each frosted section, at least some of the light striking the sidewall of the rod is emitted, or coupled, from the rod. The rod, which may have any cross-section that permits total internal reflection, can have a uniform cross-section along its length, or can monotonically decrease in size. In addition, the distal end 340 of the rod 300 can either be rounded and frosted to prevent light loss, or can be mirrored to cause the light to be retroreflected back up the rod, allowing transmission through the sidewall of the rod as described above. Because the end segment of the rod is a special case, where real coupling can be significantly less than theoretical coupling due to the exponential decay of the light, such mirroring or rounding and frosting can increase actual coupling to a reasonable approximation of theoretical coupling.

In at least some embodiments, the length of the frosted section increases relative to the length of the adjacent unfrosted section for each successive portion of the rod. In some arrangements, the combination of an unfrosted section and the adjacent frosted section can be thought of as a single segment 345, and the segment length remains the same along the length of the rod while the relative length of the frosted section within each segment increases for each successive segment. The amount of light transmitted by each frosted section is proportional to its length, and so the relative lengths of the various frosted sections can be expressed mathematically. Where z represents the location along the rod of length L, and P(z) represents the intensity of the light in the rod as a function of z, and the strength of the coupling due to the frosting can be continuously varied along the length of the rod in a controlled manner by varying the depth, shape and/or periodicity of the grooves in the frosting, then $\alpha(z)$ can be a coupling coefficient that describes the strength of the fractional coupling of the light per unit length from the rod by the frosting as a function of z. In addition, let Q(z) be the light power coupled out of the rod per unit length at a particular distance z along the rod. Thus $Q(z)=\alpha(z)P(z)$, and the objective is to determine the function $\alpha(z)$ that will produce the desired uniform distribution of light Q(z) coupled out of the rod at the various frosted sections For incoherent light and assuming conservation of energy, we have $$dP(z)/dz = -Q(z) = -\alpha(z)P(z) \qquad [\text{Eq. (1)}]$$

with the boundary condition $P(0)=P_o$.

Solving for the $\alpha(z)$ that will produce a uniform Q(z) in Eq. (1), Q(z) is set equal to $Q_o$ as is the boundary condition P(L)=0. The solutions are:

$$Q(z)=Q_o=P_o/L$$

$$P(z)=P_o(1-z/L)$$

$$\alpha(z)=L^{-1}(1-z/L)^{-1} \qquad [\text{Eqs. (2)}]$$

It will be appreciated that the dynamic range that can be achieved for $\alpha(z)$ is limited in real systems, and there will be some maximum value $\alpha_{max}$ that cannot be exceeded. Thus the high values of $\alpha(z)$ as z/L approaches 1 prescribed by Eqs (2) cannot be obtained and there will be some deviation from ideal behavior. This will manifest itself as a dip in the value of Q(z), the light power coupled out per unit length near the very end of the rod.

In those cases where the span of values that can be achieved for $\alpha(z)$ needs to be adjusted higher or lower, it is possible to do such by selecting a different diameter for the light rod. This will alter the number of reflections each light ray will undergo per unit length of the rod and thus, assuming that the properties of the frosting do not change, $\alpha(z)$ will scale inversely proportionally to the rod diameter. For rods having N segments of uniform length, where $F_i$ represents the fractional light power coupled out of the $i^{th}$ segment and index i=1 at the first segment and equals N at the last segment, the above equations simplify to $$Q_i = Q_o = P_o/N$$

$$P_i = P_o(N+1-i)/N$$

$$F_i = (N+1-i)^{-1} \qquad \text{[Eqs. (3)]}$$

Following are tables that present the entire solutions of Eqs. 3 for N=2, N=5, N=10, and N=20, where
i=segment index;
$P_i$=incident light power;
$Q_i$=coupled out light power;
$P_{i+1}$=transmitted light power; and
$F_i$=fractional light power coupled out
For N=2:

| i | $P_i$ | $Q_i$ | $P_{i+1}$ | $F_i$ |
|---|---|---|---|---|
| 1 | 1.0000 | 0.5000 | 0.5000 | 50.00% |
| 2 | 0.5000 | 0.5000 | 0.0000 | 100.00% |

For N=5:

| i | $P_i$ | $Q_i$ | $P_{i+1}$ | $F_i$ |
|---|---|---|---|---|
| 1 | 1.0000 | 0.2000 | 0.8000 | 20.00% |
| 2 | 0.8000 | 0.2000 | 0.6000 | 25.00% |
| 3 | 0.6000 | 0.2000 | 0.4000 | 33.33% |
| 4 | 0.4000 | 0.2000 | 0.2000 | 50.00% |
| 5 | 0.2000 | 0.2000 | 0.0000 | 100.00% |

For N=10:

| i | $P_i$ | $Q_i$ | $P_{i+1}$ | $F_i$ |
|---|---|---|---|---|
| 1 | 1.0000 | 0.1000 | 0.9000 | 10.00% |
| 2 | 0.9000 | 0.1000 | 0.8000 | 11.11% |
| 3 | 0.8000 | 0.1000 | 0.7000 | 12.50% |
| 4 | 0.7000 | 0.1000 | 0.6000 | 14.29% |
| 5 | 0.6000 | 0.1000 | 0.5000 | 16.67% |
| 6 | 0.5000 | 0.1000 | 0.4000 | 20.00% |
| 7 | 0.4000 | 0.1000 | 0.3000 | 25.00% |
| 8 | 0.3000 | 0.1000 | 0.2000 | 33.33% |
| 9 | 0.2000 | 0.1000 | 0.1000 | 50.00% |
| 10 | 0.1000 | 0.1000 | 0.0000 | 100.00% |

For N=20

| i | $P_i$ | $Q_i$ | $P_{i+1}$ | $F_i$ |
|---|---|---|---|---|
| 1 | 1.0000 | 0.0500 | 0.9500 | 5.00% |
| 2 | 0.9500 | 0.0500 | 0.9000 | 5.26% |
| 3 | 0.9000 | 0.0500 | 0.8500 | 5.56% |
| 4 | 0.8500 | 0.0500 | 0.8000 | 5.88% |
| 5 | 0.8000 | 0.0500 | 0.7500 | 6.25% |
| 6 | 0.7500 | 0.0500 | 0.7000 | 6.67% |
| 7 | 0.7000 | 0.0500 | 0.6500 | 7.14% |
| 8 | 0.6500 | 0.0500 | 0.6000 | 7.69% |
| 9 | 0.6000 | 0.0500 | 0.5500 | 8.33% |
| 10 | 0.5500 | 0.0500 | 0.5000 | 9.09% |
| 11 | 0.5000 | 0.0500 | 0.4500 | 10.00% |
| 12 | 0.4500 | 0.0500 | 0.4000 | 11.11% |
| 13 | 0.4000 | 0.0500 | 0.3500 | 12.50% |
| 14 | 0.3500 | 0.0500 | 0.3000 | 14.29% |
| 15 | 0.3000 | 0.0500 | 0.2500 | 16.67% |
| 16 | 0.2500 | 0.0500 | 0.2000 | 20.00% |
| 17 | 0.2000 | 0.0500 | 0.1500 | 25.00% |
| 18 | 0.1500 | 0.0500 | 0.1000 | 33.33% |
| 19 | 0.1000 | 0.0500 | 0.0500 | 50.00% |
| 20 | 0.0500 | 0.0500 | 0.0000 | 100.00% |

As noted previously, the distal end (the last segment) is a special case, where beveling, rounding or other shaping can be used to achieve nearly 100% coupling as well as coupling out any light propagating ballistically down the rod 300.

For segments of uneven length, the outcome is substantially the same, where the light output of any segment is determined by comparing the length of a given segment to the average segment length. Stated mathematically, let $L_i$ be the physical length of the ith segment. Since the overall length of the rod is L, $$L = \sum_{i=1}^{N} L_i \qquad \text{[Eq. (4)]}$$

where $\Sigma$ denotes the sum over all segments, that is all values of i from 1 thru N. In order to produce a distribution of coupled out power that is uniform over the physical length of the rod, it is necessary to scale the values of $Q_i$, the light power that is coupled out of the $i^{th}$ segment, by $L_i/L_{av}$ where $L_{av}$ is the average segment length given by $L_{av}=L/N$. The solutions of Eq. (3) then become:

$$Q_i = (L_i/L_{av})(P_o/N) = (L_i/L)P_o \qquad \text{[Eqs. (5)]}$$

$$P_i = P_o - \sum_{k=1}^{i-1} Q_k$$

$$F_i = Q_i/P_i,$$

where $\Sigma$ denotes the sum of all of the values of $Q_k$ coupled out previously in segments k=1 thru k=i−1. The numerical evaluations of Eqs. (5) are easily obtained using a spreadsheet that starts with the known values for i=1 of $Q_1=(L_1/L)P_o$, $P_1=P_o$, and $F_1=L_1/L$ and then fills in each line for higher values of i based on the values from the proceeding line.

As a specific example, consider the case of a rod with 10 segments, nine of which have length 1 and one of which (the 3rd segment) has length 3. The results are shown in the table below. Examination of the results shows that the coupled out light power $Q_3$ for the 3rd segment is three times as high as the power coupled out by the other segments, as expected.

| i (Segment Index) | $L_i$ (Segment Length) | $L_i/L_{av}$ | $P_i$ (Incident Light Power) | N = 10 $Q_i$ (Coupled Out Light Power) | $P_{i+1}$ (Transmitted Light Power) | $F_i$ (Fractional Light Power Coupled Out) |
|---|---|---|---|---|---|---|
| 1 | 1 | 0.08333 | 1.0000 | 0.0833 | 0.9167 | 8.33% |
| 2 | 1 | 0.08333 | 0.9167 | 0.0833 | 0.8333 | 9.09% |
| 3 | 3 | 0.25000 | 0.8333 | 0.2500 | 0.5833 | 30.00% |
| 4 | 1 | 0.08333 | 0.5833 | 0.0833 | 0.5000 | 14.29% |
| 5 | 1 | 0.08333 | 0.5000 | 0.0833 | 0.4167 | 16.67% |
| 6 | 1 | 0.08333 | 0.4167 | 0.0833 | 0.3333 | 20.00% |
| 7 | 1 | 0.08333 | 0.3333 | 0.0833 | 0.2500 | 25.00% |
| 8 | 1 | 0.08333 | 0.2500 | 0.0833 | 0.1667 | 33.33% |
| 9 | 1 | 0.08333 | 0.1667 | 0.0833 | 0.0833 | 50.00% |
| 10 | 1 | 0.08333 | 0.0833 | 0.0833 | 0.0000 | 100.00% |

The practical effects of the mathematical descriptions given above can be appreciated from FIGS. 3B and 3C, which show, respectively, where FIG. 3B shows segments of uniform length while FIG. 3C shows segments of uneven length, in which segment $N_3$ is twice as long as the other segments. The hatched portions represent the frosted sections of each segment, where light is coupled out. Thus, for FIG. 3B and equal length segments, the coupling is as shown in the table for N=5. But, for the design of FIG. 3C, where $N_3$ is twice as long as the other segments, the equivalent number of segments is six, and $N_3$ couples out ⅓+¼ of the light, or a total of 48.3% across the longer segment.

It will be appreciated by those skilled in the art that, while the rod 300 is shown as a consistent diameter down its length, other shapes and cross-sections of light rods are also acceptable. Thus, for example, tapered light rods can also be used in at least some embodiments. Likewise, the light rod 300 need not be straight in some embodiments, and instead can be curved in any suitable arrangement. Non-circular cross-sections, while harder to manufacture in some cases, may offer more uniform light distribution characteristics along the length of the rod in some embodiments. Further, while the frosting is assumed to be identical for each segment in the foregoing calculations and examples, in some embodiments it is desirable to vary the optical properties of the frosting at each segment. Such variations in the frosting provides a means to extend the dynamic range over which the coupling can be varied. Likewise, the variation in the frosting does not need to be continuous. Having a few discrete values, such as "weak", "medium" and "strong", offers benefit in some embodiments, while continuously variable frosting allows fine tuning of the fractional power coupled out by each segment.

Figure 4A:
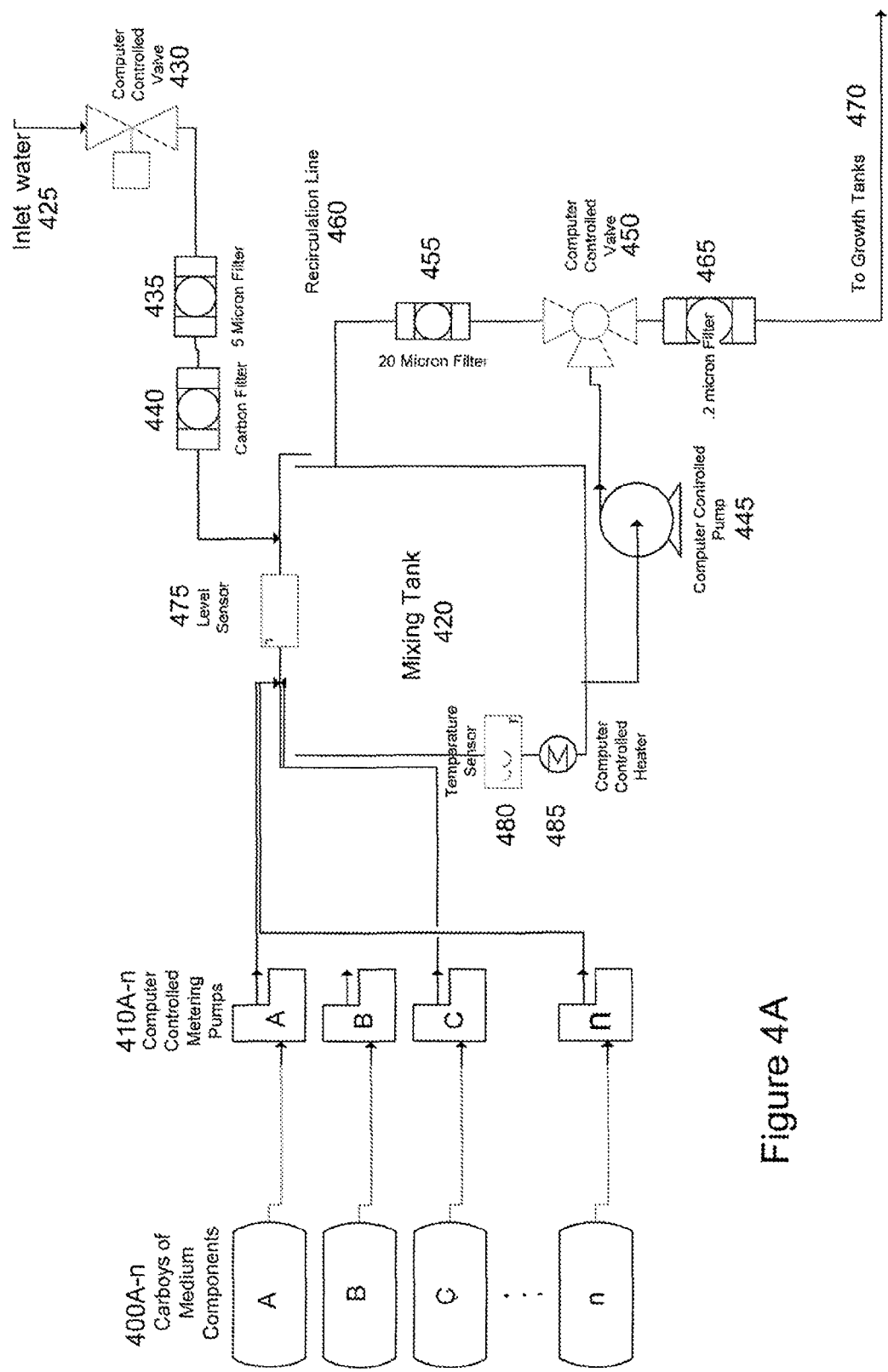
FIG. 4A shows an embodiment of a nutrient system in accordance with an aspect of the invention.
Figure 4B:
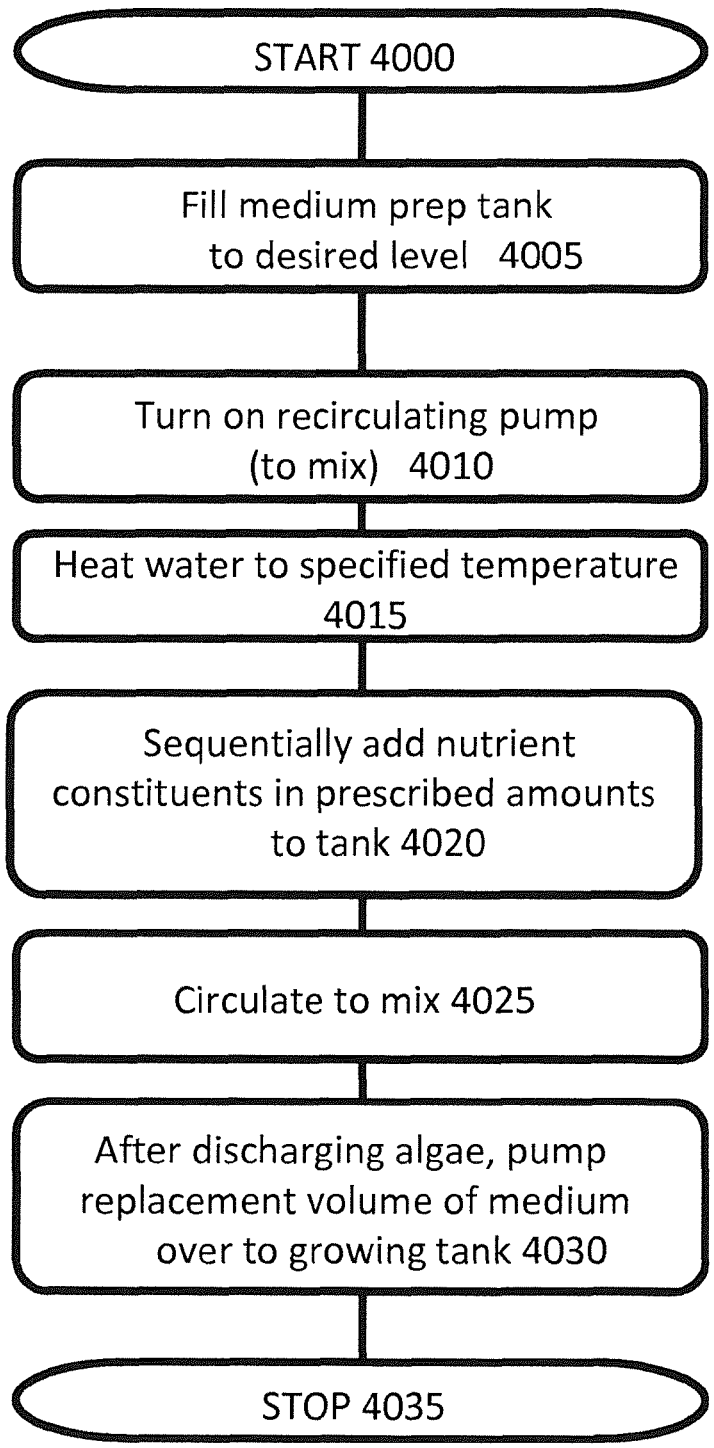
FIG. 4B shows in flow diagram form the operation of an embodiment of the nutrient system in accordance with one aspect of the invention.

Referring next to FIGS. 4A-4B, the nutrient system for supplying a regulated nutrient stream to the algae growing in the PBR can be better appreciated. A plurality of carboys 400A-n, each containing a component of a predetermined nutrient mix appropriate for a specific strain of algae, are associated with a plurality of metering pumps 410A-n, each of which is computer controlled. The metering pumps thus supply a desired mix of nutrients into a mixing tank 420, which receives water 425 via a computer controlled valve 430. A number of filters 435 and 440 can also be installed between the inlet water and the mixing tank; for example, five micron and carbon filters, respectively.

The outlet of the mixing tank is supplied to a computer controlled pump 445, which supplies the mixed nutrient stream to a computer controlled valve 450. The valve 450 directs the nutrient mix either to be recirculated in the tank via recirculation line 460 or to be supplied to an associated PBR or group of PBR's as indicated at 470. Filters 455 and 465, which can, for example, be two micron filters, can be provided on the recirculate and PBR tank lines, respectively.

With particular reference to FIG. 4B, the process for preparing the growth medium using the system of FIG. 4A can be better appreciated. The process starts at step 4000, and at step 4005 the tank 420 is filled with water to a predetermined level as determined by level sensor 475, after which the pump 445 is turned on and configured to recirculate the tank contents by valve 450 as shown at step 4010. At step 4015, the water in the tank is heated by heater 485 to a predetermined temperature as measured by temperature sensor 480. The nutrient constituents appropriate for the particular growth medium being developed are the supplied to the tank from carboys 400A-n via their associated metering pumps 410A-n at step 4020. The constituents of the growth medium can vary with the particular algae strain for which the growth medium is intended. The mix of water and nutrients is then circulated, as shown at step 4025, until the nutrients are uniformly distributed, after which the growth medium is supplied to an associated PBR at step 4030. The process either completes, as shown at step 4030, or loops back to step 4005 to begin again.

Referring next to FIGS. 5A-5B, a multi-phasic pond in accordance with an aspect of the invention can be better appreciated. FIG. 5A shows a pond 500 with a paddlewheel 505 in top plan view, and also shows the location across which the cross-sectional view of FIG. 5B is taken. FIG. 5B shows the various strata of the pond. In particular, an anaerobic zone 510 is located at the bottom of the pond. An anaerobic/aerobic transition zone 515 is located above the anaerobic zone, at the top of which are disposed one or more $CO_2$ supply tubes 520. The $CO_2$ supply tubes are typically porous tubing for distributing $CO_2$ substantially uniformly across at least a substantial portion of the pond 500. The CO2 is utilized by aerobic bacteria in an aerobic zone 525. The paddlewheel 505 creates a flow, shown from left to right in exemplary FIG. 5B, such that mixing of the effluent being remediated across the various zones is facilitated. In ponds or lagoons having only an aerobic zone, the tubes 520 can be arrayed on the bottom of the pond or lagoon.

Referring next to FIG. 6, a bubble column with internal lighting in accordance with an aspect of the invention can be better appreciated. In some instances, it is desirable to study the growth of algae or other flora in a carefully controlled environment, such as for research. In such instances, it is sometimes desirable to ensure appropriately controlled illumination and nutrient supplies, while not circulating the growth medium or growing species in a larger tank. For such implementations, the bubble column of FIG. 6 is appropriate. A tank 600 has a sealed bottom and has disposed therein at least one light rod 605 of the type described in connection with FIGS. 3A-3C. Although a round tank 600 is shown, the tank need not be round in all instances, and instead can be any convenient shape. The light rod can be centrally disposed or disposed asymmetrically, and can be configured together with the shape of the tank to provide whatever uniformity of illumination or lack thereof is desired. In an embodiment, the position of the light rod can be varied within the tank to facilitate different illumination patterns. Compressed air or other gases, utilized in the manner described in connection with FIGS. 2A-2B et seq., are supplied to a diffuser 610 located at the bottom of the tank via a tube 615, which can either enter the tank from the bottom or down an inside wall as shown. The diffuser can be configured to supply gas uniformly across the bottom of the tank or in any desired pattern, but the sole agitation and mixing is through the upward movement of the bubbles through the algae-laden medium, since there is no larger tank for creating the upward and downward flows of the systems shown in FIGS. 2A-2F. In at least some embodiments, a supply tube 620 is provided by which algae can be introduced to the column. The supply tube 620 can be located at any convenient position on the tank, including a lid 625, or an orifice in the lid through which the light rod 605 passes, a sidewall, or the bottom of the tank.

In operation, the bubble column is filled with a growth medium, and algae strains are introduced. A gas mixture appropriate for the particular study being conducted is introduced via the diffuser, and the resulting bubbles entrain the algae as described above. However, because the bubble column is not contained within an outer housing or tank, the fluid levels are typically maintained at levels below overflowing in most embodiments.

Referring next to FIG. 7, an alternative embodiment of a wastewater remediation system in accordance with an aspect of the invention is shown in schematic form. Organic waste 700 is supplied to an anaerobic digester 705, which begins the breakdown process and generates methane 710 and an effluent stream 715, comprised in part of $CO_2$, nitrogen, phosphorus and other constituents. The effluent is supplied to a multiphasic pond 720, together with water 725 as needed. The methane provides fuel for a generator/boiler 730, which generates heat 735 that is supplied back to the anaerobic digester 705. The generator 730 also provides $CO_2$ 740 to a photobioreactor 745, typically constructed in accordance with the aforementioned teachings, as well as the multiphasic pond 720. The generator 730 also supplies electricity and heat 750 to both the PBR 745 and the multiphasic pond 720, and may in some implementations supply additional electricity at 775. The pond 720 receives additional atmospheric CO2 at 760, if needed, and outputs remediated wastewater. The remediated wastewater can then be given an optional final treatment, as shown at 765, such as an ultraviolet polish, carbon filtration, or other remediation step. In some embodiments, the pond 720 can also generate usable biomass as shown at 770.

Figure 8A:
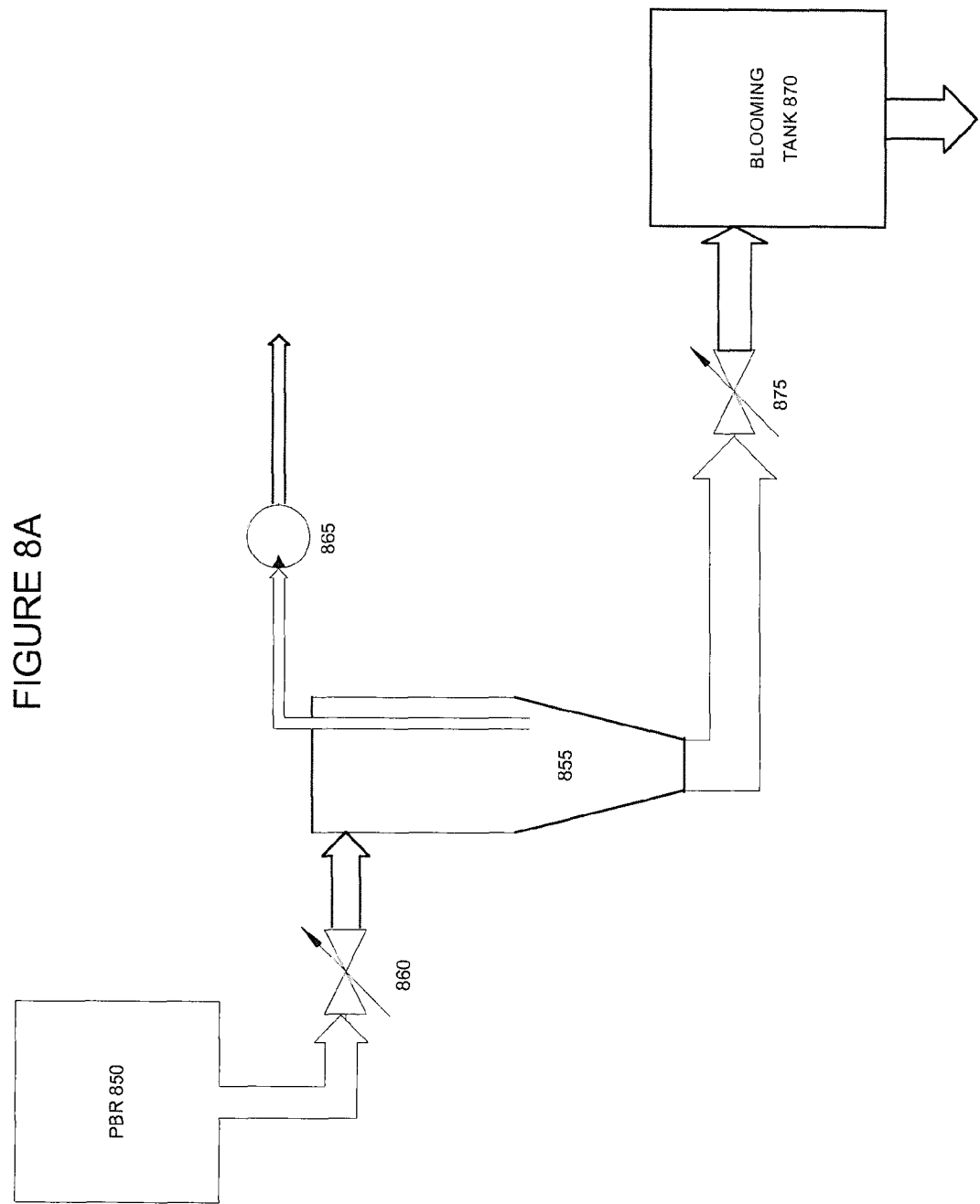
FIGS. 8A-8B show in system and flow diagram forms a concentrator process in accordance with an aspect of the invention.
Figure 8B:
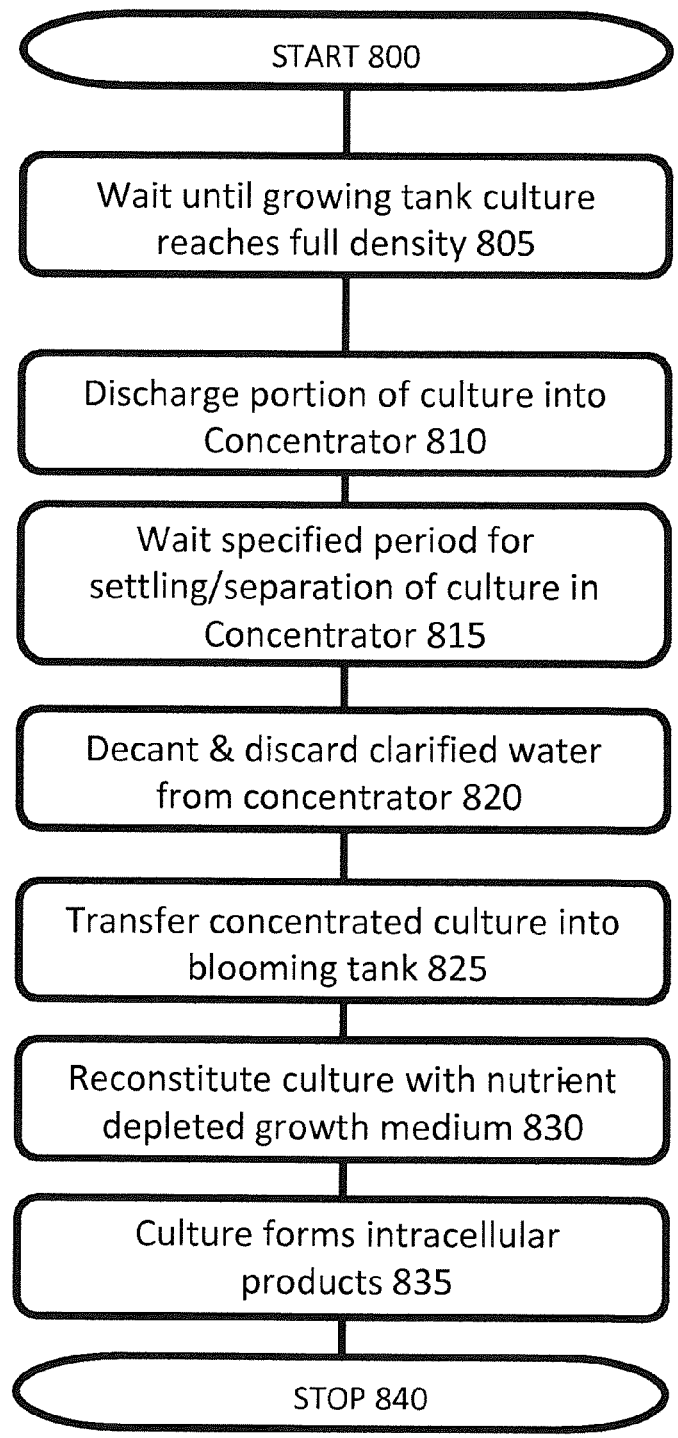

Referring next to FIGS. 8A-8B, a concentrator system and process can be better appreciated. Some species of algae grow best under one set of conditions, but produce desired products more rapidly under different conditions. One example is algae that grows best when supplied with nitrogenous nutrients, but produces higher concentrations of lipids when deprived of nitrogenous nutrients. To maximize the productivity of a system, it is desirable to create different growing conditions to achieve the different goals, and also to achieve the transition as quickly as possible. As shown in FIGS. 8A-8B, algae of a desired species is grown to a desired density at step 800 in a PBR 850 using a first growth medium designed to achieve high algae density as promptly as possible. Once the density level has been achieved, at least a portion of the algae is transferred to a concentrator tank 855, as shown at step 810, typically although not necessarily through a computer-controlled valve 860. The transfer process requires that a substantial amount of the first growth medium be transferred with the algae, to prevent damage to the algae.

After transfer to the concentrator tank 855, the combination of algae and the first growth medium are allowed to settle as shown at step 815, causing the growth medium, which is largely water, to clarify. Then, at step 820, the clarified growth medium is removed, either from the top of the concentrator or any other suitable location that will not remove and/or damage the algae within the concentrator 855. It will be appreciated that not all of the first growth medium can be removed, but a significant percentage, in the range of 75%, can be removed without damaging the algae. Then, at step 825, the remaining growth medium and the algae are transferred to a blooming tank 870 through a valve 875, also typically but not necessarily computer-controlled. A second growth medium is used in the blooming tank 870, formulated to stimulate development of the desired products, as shown at step 830. It will be appreciated that, in at least some embodiments, the second growth medium is added to the blooming tank in advance of the transfer of the algae into the blooming tank, to minimize physical damage to the algae during transfer, although these steps can be reversed depending upon the particular algae, the amount of first growth medium remaining after step 820, and the trauma likely to be suffered by the algae during the transfer process. To facilitate a smooth transfer with minimal trauma to the algae, a concentrator tank 855 having a funnel-shaped lower portion can be used, where the algae settles in the funnel-shaped portion both to permit easy removal of the first growth medium and to permit easy transfer to the blooming tank. Once the algae and second growth medium are combined in the blooming tank 870, the process waits until adequate amounts of the desired products are produced by the algae, at which point those products are removed for further use, and shown at step 835. The blooming tank can be configured in substantially the same way as the PBR 850, and in some implementations the PBR 850 can be re-used as the blooming tank.

In use, the first growth medium can, for example, be nitrogen-rich and thus encourage rapid growth of selected algae. The transfer to the concentrator and removal of the first growth medium rapidly reduces the levels of nitrogen and other nutrients, including trace elements, in the algae. Then, the second growth medium can be, for example, pure water, or nitrogen-depleted. At this point the selected algae begin to produce lipids or other products which can be used, for example, as biofuels. The result, and benefit, of the concentration process is that it rapidly accelerates the depletion of nutrients in the growth medium which, in turn, accelerates the generation of the desired products. For example, if the concentration process were not used, the desired depletion of nitrogen in the first growth medium could take in the range of ten days, during which time the rate of algae growth would be substantially sub-optimal, while at the same time the algae would not be producing the desired levels of usable products. By comparison, the concentration process of the present invention can be accomplished within minutes or, at most, hours, such that the beginning of production occurs much more rapidly, resulting in increased efficiency and lower operating costs.

Inevitably, power failures will occur regardless of the quality of backup systems. Algae is somewhat fragile, and loss of power for extended periods will kill the algae being grown in the PBR's and blooming tanks. To prevent unnecessary loss of algae in the event of a power failure, it is desirable to provide a soft-fail sequence by which the life of the algae is prolonged for as long as possible. A soft-fail process is described in FIG. 9, where a check is made at step 905 to determine whether power is at proper levels. If yes, the process loops so that checking for power failures is essentially continuous. If power is not at proper levels, the process advances to step 910 and any preparation of growth medium is halted, as is any algae transfer or discharge. In addition, as shown at step 915, the LED's are turned off. Further, at step 920, the temperature tolerances set into the control system are automatically expanded. Still further, the pH target in the tank is adjusted for the particular species being grown to maximize culture viability, as shown at step 925. Finally, the gas stream is switched from continuous operation to intermittent, so that mixing in the tank continues although not at the same levels. It will be appreciated that steps 910 to 930 can be performed either essentially concurrently, or in stages where the time increment between each step can be adjusted depending upon the particular operating conditions, the strain(s) of algae, and the projected time before power is restored. Finally, as shown at step 935, the state of the power is tested again. If power has been restored, the operations of steps 910-930 are restored to normal conditions as shown at step 940. If power has not been restored, the check continues until power is restored or reserve power is lost.

From the foregoing, it can be appreciated that new and novel bioremediation systems and methods have been described, with novel aspects regarding illumination, nutrient supply and mixing, algae growth processes, generation of biomass and other products, and soft failure processes. Having fully described a preferred embodiment of the invention and numerous alternatives of the various aspects of the invention, those skilled in the art will recognize, given the teachings herein, that numerous alternatives and equivalents exist which do not depart from the invention. It is therefore intended that the invention not be limited by the foregoing description, but only by the appended claims.

We claim:

1. A photobioreactor for growing algae, comprising:
   a tank to contain algae and growth medium for the algae;
   at least one light pipe to provide light in the tank for accelerating algae growth in the tank, the light pipe comprising a light source located outside of the tank for generating and emitting light and a light rod having a distal longitudinal end disposed inside the tank and a proximal longitudinal end disposed to receive light emitted from the light source to be delivered from the light rod into the tank to provide light for accelerating algae growth in the tank;
   the light rod having alternating frosted and unfrosted portions located in the tank and spaced along a longitudinal length of the light rod between the proximal end and the distal end, the unfrosted portions having a transverse cross-section that permits total internal reflection of light in the unfrosted portions wherein light in the light rod from the light source is transmitted along the unfrosted portions by total internal reflection and in the frosted sections a portion of the light from the light source is emitted from the light rod in the tank.

2. The light pipe of claim 1 wherein the light source is an LED.

3. The photobioreactor of claim 1 wherein the distal end of the light rod is rounded.

4. The photobioreactor of claim 1 wherein the distal end of the light rod is frosted.

5. The photobioreactor of claim 1 wherein the distal end of the light rod opposite the proximal end is reflective.

6. The photobioreactor of claim 1 wherein the frosted portions of the light rod are disposed in a volume of algae growth medium contained within the tank.

7. A bioremediation system comprising:
   the photobioreactor claim 1,
   a nutrient system for supplying sufficient growth medium to the photobioreactor to enable continuous growth in the photobioreactor of selected strains of algae,
   a multiphasic remediation lagoon or pond adapted to receive organic waste for remediation and also to receive, from the photobioreactor, inoculations of the selected strains of algae.

8. The bioremediation system of claim 7 wherein the multiphasic pond comprises at least an anaerobic zone and an aerobic zone, and means for creating substantially consistent directional fluid flow within the pond.

9. The bioremediation system recited in claim 7 comprising a nutrient system, the nutrient system comprising:
   a mixing tank;
   a recirculation line having an input fluidically coupled with the mixing tank and having an output fluidically coupled with the mixing tank;
   an output line having an input fluidically coupled with the mixing tank and having an output fluidically coupled with the photobioreactor,
   a plurality of reservoirs, each reservoir containing a volume of a nutrient constituent appropriate for growth of a specific strain of algae;
   a plurality of metering pumps, respective ones of the plurality of metering pumps fluidically coupled with the mixing tank and with respective ones of the plurality of reservoirs; and
   a computer control system having:
      instructions to introduce a plurality of distinct nutrient constituents from the reservoirs into a volume of water in the mixing tank in relative volumes appropriate for growth of the specific strain of algae;
      instructions to recirculate contents of the mixing tank by flowing the contents through the recirculation line to mix the distinct nutrient constituents until a mixture of the water and the nutrients is substantially uniformly distributed; and
      instructions to supply the mixture to the photobioreactor by flowing the mixture over the output line.

10. The bioremediation system recited in claim 9 wherein the nutrient system comprises:
   a heater disposed to heat fluid in the mixing tank; and
   a temperature sensor, wherein the computer control system has instructions to initiate introduction of the plurality of nutrient constituents after the temperature sensor indicates a temperature of the water is substantially at a predetermined temperature.

11. A method for growing a specific strain of algae, the method comprising in the bioremediation system of claim 9:
   introducing a plurality of the distinct nutrient constituents in relative volumes appropriate for growth of the particular strain of algae from the reservoirs into a volume of water in the mixing tank;
   recirculating contents of the mixing tank through the recirculation line to mix the plurality of the distinct nutrient constituents until a mixture of the water and the plurality of the distinct nutrient constituents is substantially uniformly mixed; and
   supplying the substantially uniformly mixed mixture to the photobioreactor by flowing the mixture over the output line.

12. The method recited in claim 11 further comprising filtering fluid along the output line.

13. The method recited in claim 11 further comprising:
heating fluid in the mixing tank; and
measuring a temperature of fluid in the mixing tank, wherein introducing the plurality of distinct nutrient constituents is performed when a temperature of the water is substantially at a predetermined temperature.

14. A method for remediating waste streams comprising: providing an anaerobic digester region for performing a first remediation step, the anaerobic digester generating combustible gas and an effluent stream,
combusting the gas to generate heat, electricity, and $CO_2$,
supplying a portion of the heat, electricity and $CO_2$ generated by the combusting step to the photobioreactor of claim 1,
supplying another portion of the heat, electricity and $CO_2$ generated by the combusting step to a multiphasic pond,
supplying to the multiphasic pond the effluent stream and dense algae produced by the photobioreactor.

15. The photobioreactor of claim 1, comprising;
a plurality of said light pipe;
at least one cooling fan positioned to direct air flow to cool the light sources during operation.

16. The photobioreactor of claim 15, comprising an air dome covering the light sources and into which the at least one fan directs air flow to cool the light sources during operation.

17. The photobioreactor of claim 15, where each said light pipe comprise a heat exchanger thermally coupled to the said light source to assist cooling the said light source by air flow from the at least one fan.

18. The photobioreactor of claim 1, comprising a plurality of said light pipe with spacing between the light rods in a range of from 10 to 15 centimeters.

19. A method for growing algae in the photobioreactor according to claim 1, the method comprising;
containing a mixture of algae and growth medium for the algae in the tank;
generating light by the light source and receiving generated light from the light source by the light rod;
emitting portions of the generated light from the light rod into the mixture in the tank through the frosted portions of the light rod.

* * * * *